United States Patent
Nichols

(10) Patent No.: US 10,803,538 B2
(45) Date of Patent: Oct. 13, 2020

(54) SYSTEM AND METHOD FOR AUTOMATED DATA ENTRY AND WORKFLOW MANAGEMENT

(71) Applicant: Optum, Inc., Minnetonka, MN (US)

(72) Inventor: Matthew Nichols, Buffalo, MN (US)

(73) Assignee: Optum, Inc., Minnetonka, MN (US)

( * ) Notice: Subject to any disclaimer, the term of this patent is extended or adjusted under 35 U.S.C. 154(b) by 805 days.

(21) Appl. No.: 14/686,406

(22) Filed: Apr. 14, 2015

(65) Prior Publication Data

US 2015/0294089 A1 Oct. 15, 2015

Related U.S. Application Data

(60) Provisional application No. 61/979,296, filed on Apr. 14, 2014.

(51) Int. Cl.
| | | |
|---|---|---|
| *G06Q 50/22* | (2018.01) | |
| *G16H 40/20* | (2018.01) | |
| *G06F 3/01* | (2006.01) | |
| *G06F 3/0484* | (2013.01) | |
| *G16H 40/63* | (2018.01) | |
| *G06F 3/03* | (2006.01) | |
| *G06F 3/16* | (2006.01) | |
| *G16H 10/20* | (2018.01) | |
| *G16H 10/60* | (2018.01) | |

(52) U.S. Cl.
CPC .............. *G06Q 50/22* (2013.01); *G06F 3/011* (2013.01); *G06F 3/0304* (2013.01); *G06F 3/0484* (2013.01); *G06F 3/167* (2013.01); *G16H 10/20* (2018.01); *G16H 40/20* (2018.01); *G16H 40/63* (2018.01); *G16H 10/60* (2018.01)

(58) Field of Classification Search
CPC ...... G06F 3/011; G06F 3/0304; G06F 3/0484; G06F 3/167; G16H 10/20; G16H 10/60; G16H 40/20; G16H 40/63
See application file for complete search history.

(56) References Cited

U.S. PATENT DOCUMENTS

| | | |
|---|---|---|
| 6,915,254 B1 | 7/2005 | Heinze et al. |
| 7,908,552 B2 | 3/2011 | Heinze et al. |
| 8,682,823 B2 | 3/2014 | Heinze et al. |
| 9,063,924 B2 | 6/2015 | Heinze et al. |
| 2004/0093239 A1* | 5/2004 | Ott .......................... G16H 15/00 705/2 |
| 2005/0187948 A1* | 8/2005 | Monitzer ................. G06F 19/00 |
| 2009/0070140 A1 | 3/2009 | Morsch et al. |
| 2010/0082371 A1* | 4/2010 | Kamp ..................... G16H 10/60 705/3 |
| 2011/0202370 A1* | 8/2011 | Green, III .............. G06Q 50/24 705/3 |
| 2013/0030826 A1* | 1/2013 | Blom ..................... G06Q 10/10 705/2 |

(Continued)

*Primary Examiner* — Neal Sereboff
(74) *Attorney, Agent, or Firm* — Dorsey & Whitney LLP

(57) ABSTRACT

A system and method that provides for integrated data entry and workflow capabilities through one or more computing devices provided to personnel who work at various stations throughout a facility. Automated identification, record updates, workflow management, and alerts are facilitated through the computing devices, which include a headset that includes one or more input devices such as a microphone, a speaker, a camera, and/or a visual display device.

18 Claims, 21 Drawing Sheets

(56) References Cited

U.S. PATENT DOCUMENTS

| | | | |
|---|---|---|---|
| 2013/0218721 A1* | 8/2013 | Borhan | G06Q 30/02 |
| | | | 705/26.41 |
| 2014/0222526 A1* | 8/2014 | Shakil | G06F 19/3456 |
| | | | 705/7.38 |
| 2014/0276239 A1* | 9/2014 | Subramaniam | A61B 5/0022 |
| | | | 600/595 |
| 2014/0365242 A1* | 12/2014 | Neff | G16H 10/60 |
| | | | 705/3 |
| 2015/0066537 A1 | 3/2015 | Sheffer et al. | |
| 2015/0100333 A1* | 4/2015 | Fitzgerald | G06Q 30/018 |
| | | | 705/2 |
| 2015/0221151 A1* | 8/2015 | Bacco | G06K 9/00288 |
| | | | 340/5.83 |

\* cited by examiner

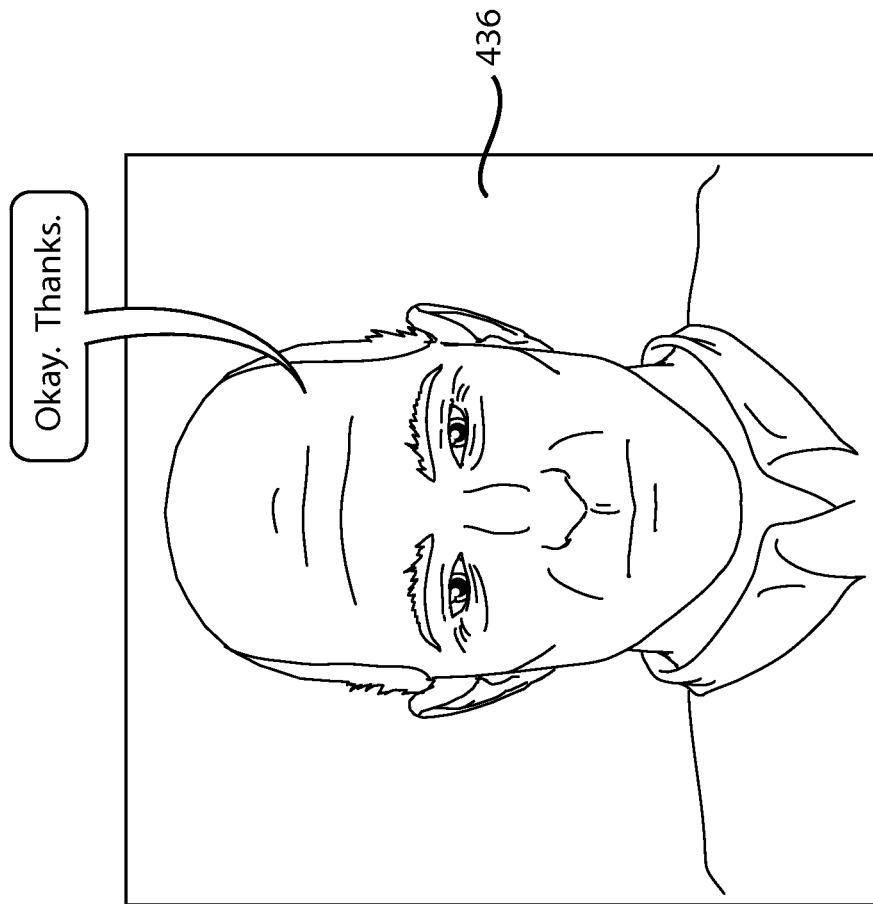

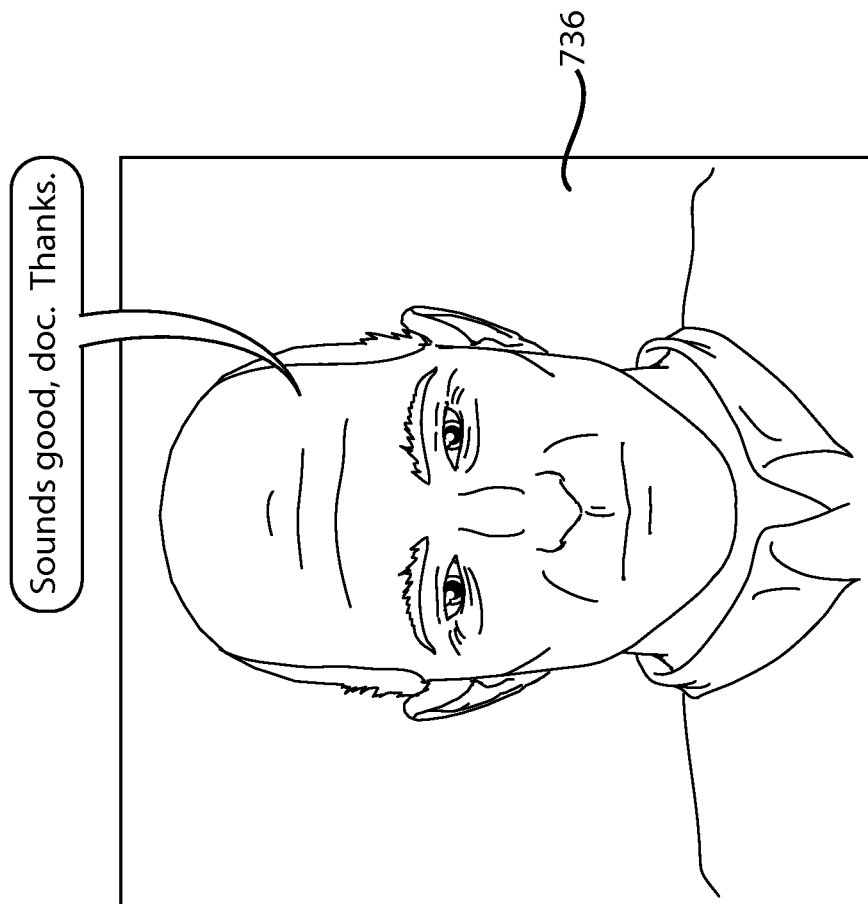

FIG. 9A

| MAIN MENU | | |
|---|---|---|
| STAGE | # | MIN |
| All | | |
| Triage | 5 | 35 |
| Reception | 2 | 10 |
| Doctor | 11 | 65 |
| Re-evaluation | 1 | 5 |
| Medication | 5 | 20 |
| Lab Results | 5 | 40 |
| Observation | 6 | 25 |

| WAITING LAB RESULTS | | |
|---|---|---|
| NAME | LAB | MIN |
| Luís Colombo | Hemogram | 40 |
| Bob Johnson | X-Ray Chest | 36 |
| José Luiz Santolaria | CT Head | 10 |
| Patrícia Azevedo | X-Ray Foot | 20 |
| Carlos Eduardo Almeida | Hemogram | 14 |

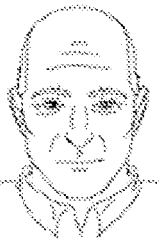

| PATIENT | | |
|---|---|---|
| | NAME | Bob Johnson |
| | GENDER | Male |
| | AGE | 67 |
| | ARRIVAL | 1:45 PM |
| | WAITING | 15 Minutes |
| | STATUS | Waiting Lab Results X-Ray Chest Hemogram |
| ALERTS | ** ALLERGIC TO LATEX ** | |
| ADDITIONAL OPTIONS | | |

| OPTIONS | |
|---|---|
| Set | "Waiting for feedback" |
| Set | "Received feedback" |
| Other | ... |

908

SYSTEM AND METHOD FOR AUTOMATED DATA ENTRY AND WORKFLOW MANAGEMENT

CROSS-REFERENCE TO RELATED APPLICATION

This application is a non-provisional of and claims priority to U.S. Provisional Application Ser. No. 61/979,296 filed on Apr. 14, 2014 and entitled "System and Method for Automated Data Entry and Workflow Management" the content of which is herein incorporated by reference in its entirety.

TECHNICAL FIELD

The technology described herein relates to systems and methods for automated data entry and workflow management.

BACKGROUND

Currently, medical facilities such as hospitals and clinics can exhibit an impersonal and bureaucratic feel due to the technology used by medical personnel during their interaction with patients. When a patient visits a hospital or clinic, the need arises to record the patient's identifying information and to ensure that the patient is accurately matched with medical records that contain their medical history and other important information needed to accurately provide care. Once the patient is admitted, there exists a continuing need to accurately and efficiently record the patient's vital statistics and disease symptoms and to ensure that these pieces of information are reliably captured in the patient's medical records. While conveying this information is needed to ensure quality care, the process of collecting and recording this information can appear cold and unfriendly as well as inefficient. Medical personnel tend to focus their attention on computer display terminals, keyboards, and other equipment during the information intake process. This tendency takes away from the type of human interaction that patients expect and that can put them at ease in the potentially stressful and uncomfortable environment of a hospital or medical clinic.

Attempts to solve this problem can lead to additional complications. In some circumstances, medical personnel can attempt to provide greater levels of human interaction by delaying the process of entering information. For example, when taking vitals or other statistics from patients, well-intentioned nurses may focus on the patient and in so doing memorize rather than immediately record the information they receive. At the end of their shift, these nurses then record the information they have memorized. Because, in some instances, this memorized information can be associated with a high number of individual patients and several hours after the interaction, inaccuracies can result in the recordation process. In other instances, hospital and medical clinic management have attempted to address this problem by employing medical "scribes" who shadow medical personnel and record patient information as it is received. While this solution alleviates the need of medical personnel to be continually entering patient information, this solution creates added costs that the hospital or medical clinic may not be able to shoulder.

Thus, there exists a need to more fully incorporate greater levels of human interaction in the process of entering medical information. These and other deficiencies of the prior art are addressed herein.

SUMMARY

Present embodiments are directed to a system and method that provides for integrated data entry and workflow capabilities. The system includes one or more computing devices that may be provided to personnel who work at various stations throughout a facility. Personnel may include healthcare professionals such as doctors, nurses, lab technicians, and administrative staff trained to admit or check-in the patient for a healthcare-related appointment. Generally, the facility is one that serves patients, customers, or other members of the public. The facility may be a clinic, hospital or a telemedical station. The computing devices include a handset or headset with one or more input devices such as a microphone, a speaker, a camera, and/or a visual display device, and the computing device may be communicatively coupled to a computing network that stores and manages data, such as healthcare data, for patients, customers, or other members of the public. As personnel who wear the device interact with customer or patients, the input devices may be used to record the customer or patient's voice and/or capture their image and to pass this data to downstream parts of the system that process the data to identify the patient or customer, bring-up records, generate or update workflow tickets, and the like. Personnel may additionally use the microphone to enter voice commands that are interpreted and executed by the system to update records, generate or modify workflow tickets, generate alerts, and the like. These and other features of the system may be executed by one or more data processing applications that implement various capabilities such as facial recognition, natural language processing, text analytics, speech-to-text, and speaker verification. Because inputs and outputs are managed through a headset or handset, personnel can maintain eye contact with the patients or customers while at the same time entering data into the system and/or receiving information from the system.

In certain implementations, a method for entering medical information with integrated data entry and workflow during an interaction with a patient may comprise receiving a special-purpose wearable computing device, associating the patient with the device, receiving information relating to the patient from a head-mounted display of the device, and causing a record of the patient to be updated by speaking a command. The device may be configured to enable a user to input and retrieve medical information without breaking line-of-sight interaction with the patient. The receiving and causing steps may be performed without breaking line-of-sight interaction with the patient.

In another implementation, a method for facilitating an improved interaction between a user and a patient may comprise receiving voice data from a remotely located special-purpose wearable computing device worn by the user, converting the voice data into text data, translating the text data to structured data using natural language processing, and updating a medical record of the patient based on the structured data.

In yet another implementation, a method for improving the flow of patients through a hospital may comprise providing a list of patients to a head-mounted display of a special-purpose wearable computing device worn by a user, receiving from the device a selection of a patient from the list of patients, providing patient information at the display responsive to receiving the selection, receiving data regarding an interaction between the user and the patient; and updating a record associated with the patient with the received data. The patient information may comprise an image of the patient usable by the user to locate the patient.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIGS. 4A through 4E illustrate an example interaction between medical personnel and a patient.

FIGS. 7A through 7E illustrate another interaction between the patient and medical personnel.

FIGS. 9A through 9D illustrate a series of screens of an implementation of a patient management system.

DETAILED DESCRIPTION

Present embodiments are directed to a system and method that provides for integrated data entry and workflow capabilities. The system includes one or more computing devices that may be provided to personnel who work at various stations throughout a facility. Generally, the facility is one that serves patients, customers, or other members of the public. The computing devices include a headset that includes one or more input devices such as a microphone, a speaker, a camera, and/or a visual display device. As personnel who wear the headset interact with customer or patients, the input devices may be used to record the customer or patient's voice and/or capture their image and to pass this data to downstream parts of the system that process the data to identify the patient or customer, bring-up records, generate or update workflow tickets, and the like. Personnel may additionally use the microphone to enter voice commands that are interpreted and executed by the system to update records, generate or modify workflow tickets, generate alerts, and the like. These and other features of the system may be executed by one or more data processing applications that implement various capabilities such as facial recognition, natural language processing, text analytics, speech-to-text, and speaker verification. Because inputs and outputs are managed through a headset, personnel can maintain eye contact with the patients or customers while at the same time entering data into the system and/or receiving information from the system.

System Architecture

Figure 1:
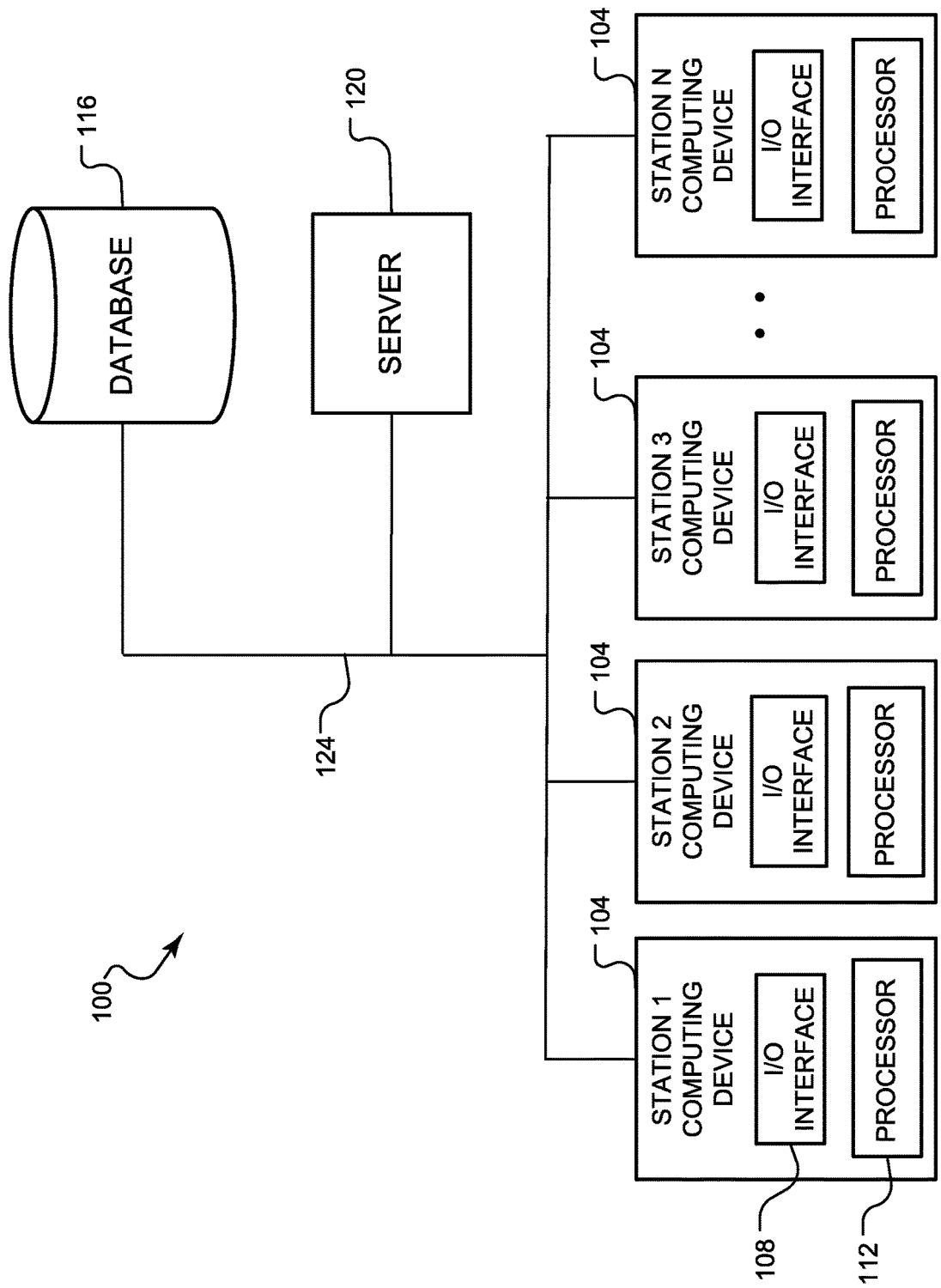
FIG. 1 is a schematic illustration of an example system architecture in accordance with embodiments discussed herein.

FIG. 1 is schematic illustration of an example system architecture in accordance with embodiments discussed herein. The example system is generally identified with reference numeral 100. The system 100 provides integrated data entry and workflow management capabilities and has particular, but not exclusive application to medical facilities. A medical facility or other environment in which the system 100 operates typically contains one or more stations that are staffed with personnel who are provided with one or more station computing devices 104. For example, a medical facility may include an admitting station such as a front desk or reception area where a patient is received when they first arrive at the facility. Other stations within a medical facility may include a lab station where various tests are performed or a vitals station where the patient's vital signs are assessed. A medical facility also typically includes a doctor visit station such a private room where a doctor assesses, diagnosis, consults or otherwise interacts with a patient.

In accordance with embodiments discussed herein, some or all of the medical personnel that are assigned to or otherwise associated with the various stations of the medical facility are provided with a computing device 104 that is adapted to enhance their ability to interact with patients. In one embodiment, the input/output interface 108 includes an audio device such as headset or earpiece that includes a speaker and a microphone. Here, medical personnel enter patient data into the system 100 by speaking into the microphone and receive patient information through audio that is output through the speaker. In another embodiment, the input/output interface 108 includes an audio-visual device such as eyeglasses or a headset that includes a speaker, a microphone, a camera and/or visual display. Here, medical personnel enter patient data into the system 100 by speaking into the microphone and receive patient information through either audio that is output through the speaker or data that is displayed on the visual display device.

Because the input/output interface 108 includes a headset or the like that is worn by medical personnel on their head or face, the ability of medical personnel to interact with patients is greatly enhanced in several respects. For example, the microphone or the camera mounted on the headset may be used to collect audio and/or video data that can be processed so that the system 100 can recognize the patient and automatically bring-up records or other information relevant to treating or otherwise caring for the patient. Relevant patient information or alerts may be output to medical personnel through the speaker or video display that is mounted on the headset. Medical personnel may also use the microphone mounted on the headset to enter voice commands that are interpreted and executed by the system 100. Here, medical personnel may enter commands to update medical records, initiate or update workflow items, generate future alerts, and so on. Because inputs and outputs are managed through a headset, medical personnel can maintain eye contact with the patient while at the same time entering patient data into the system 100 and/or receiving patient information from the system 100.

The computing device 104 may include a processor 112 that supports the function of the input/output interface 108. In one respect, the processor 112 may be configured to run computer executable code that manages the flow of data to and from the input/output interface 108. The processor 112 may additionally be configured to run applications that execute higher level data processing functions. Thus, the processor 112 may be provided in association with a computer readable storage medium that stores processor executable code. The processor executable code may be stored on a long-term basis in a non-volatile memory portion of the computer readable storage medium. The processor executable code may also be loaded into a volatile memory portion of the computer readable storage medium from another location such as from across a network 124.

The system 100 generally includes one or more applications that operate to process the data received from and sent to the input/output interface 108. Data processing applications in accordance with present embodiments may implement various capabilities such as facial recognition, natural language processing, text analytics, speech-to-text, and speaker verification. Data processing applications or portions thereof may execute locally on the processor 112 associated with the computing device 104 or may execute on one or more severs 120 that are connected to the computing device 104 across a network 124. The system 100 may additionally include one or more databases 116 that store patient data. By way of example, patient data may include electronic medical records or workflow records associated with patient's visit to the medical facility. The data processing applications, whether running locally on the processor 112 or on the server 120, may access and/or update records as the computing device 104 is operated by medical personnel in their interaction with patients.

Figure 2:
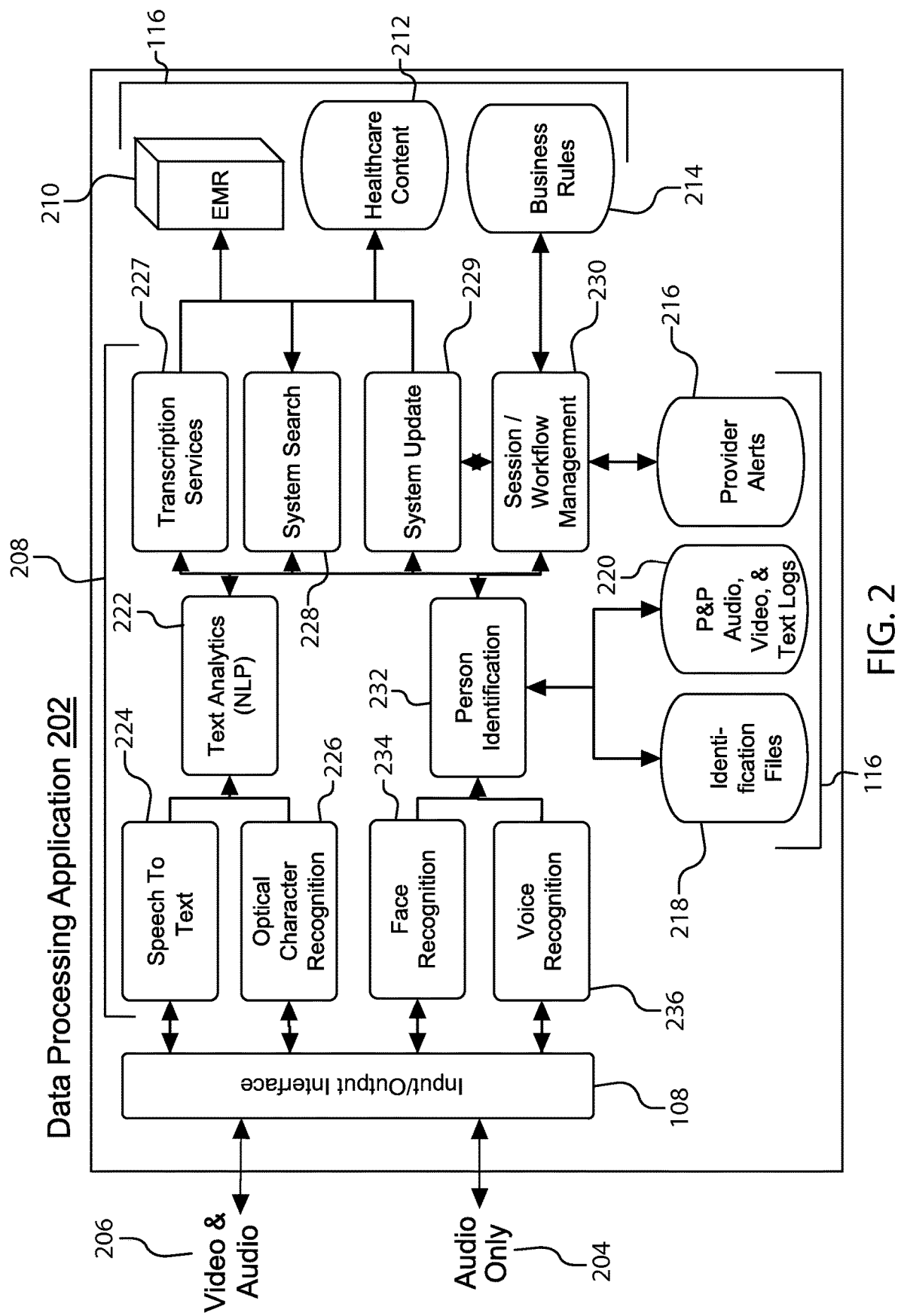
FIG. 2 is a schematic illustration of an example data processing application in accordance with embodiments discussed herein.

FIG. 2 is a schematic illustration of an example data processing application 202 in accordance with embodiments discussed herein. The data processing application 202 includes or is in communication with the input/output interface 108 that is associated with a computing device 104. As shown in FIG. 2, the input/output interface 108 may be associated with audio only equipment 204. In other embodiments, the input/output interface 108 is associated with an audiovisual input/output device 206. The data processing application 202 is generally configured to process data received from and sent to the input/output interface 108. In this regard, the data processing application 202 communicates with one or more databases 116, which store data such as patient records or workflow data associated with operation of the medical facility. The data processing application 202 includes various data processing capabilities 208 that facilitate accessing and/or updating records stored in the various databases 116 as the computing device 104 is operated by medical personnel in their interaction with patients.

As shown in FIG. 2, the data processing application 202 may communicate with an electronic medical record database (EMR) 210. The EMR database 210 includes records for the various patients that are served by the medical facility. Patient records stored in the EMR database 210 may include identifying information such as the patient's name, address, social security number, and the like. Patient records in the EMR database 210 may also include insurance information such as the patient's insurance carrier, policy number, coverage limitations, and the like. Additionally, patient records in the EMR database 210 may include medical history information that is accumulated from prior medical facility visits. This information may include known patient diseases or aliments, allergies, immunizations, current and past medications, diagnoses, procedures, and the like. The EMR database 210 may be located on-site or off-site and may be part of Health Insurance Portability and Accountability Act (HIPAA) compliant system of EMR databases that facilitate information sharing between medical facilities and portability of medical records.

The data processing application 202 may also communicate with a healthcare content database 212. The healthcare database 212 may include information that can be used by medical personnel in connection with providing care to patients. For example, the healthcare database 212 may include up-to-date information on evidence-based medicine or best practices for various medical tests and procedures. Additionally, the health care database 212 may include information on recent medical studies, up-coming conferences or training seminars, or other information that may be of interest to doctors, nurses or other medical personnel. Additionally, the healthcare database 212 may include information to share content such as prevention, monitoring, and self-care of conditions or symptoms directly with patients using a patient version of the device to enhance patient education in a private, secure manner.

The data processing application 202 may also communicate with a business rules database 214 and/or a provider alerts database 216. The business rules database 214 may include information regarding rules, policies and/or procedures that have been established for the medical facility. The business rules database 214 may contain records or other data used to manage workflows within the medical facility. The various stations within the medical facility may generate and process workflow tickets that are stored and distributed through the operation of the business rules database 214. For example, when a patient first arrives and explains the reason for his or her visit to the medical facility, the admitting station may generate a workflow ticket for tests to be performed by the lab station or vitals to be taken by the vitals station. The lab station and/or the vital station may process these tickets by performing tests and/or taking vitals and incorporating obtained information into additional tickets that are further processed by other stations, such as the doctor station. The provider alerts database 216 may store alert information that may be delivered to providers and/or patients at various stations within the medical facility through the operation of the data processing application 202. In another example, when a patient first checks-in at the admitting station, the system may query the patient's data records, such as the patient's EMR and/or health history, may apply evidence-based medicine guidelines, HEDIS rule, and/or other business rules, and the system may identify gaps in care, high risk medication warnings, low-cost alternative medications and other types of point of care information. The system may generate a workflow for the encounter based on the query, and for example, the workflow may include the step of: alerting a doctor of high risk medications the patient is prescribed, sending the patient to visit a lab for a blood draw to close gaps in care, and/or alerting the nurse or doctor of low-cost alternative medications available to the patient.

The data processing application 202 may also communicate with an identification files database 218 and/or a log database 220. As mentioned above, the system 100 may be configured to automatically recognize patients through audio and/or video data collected through a microphone or camera associated with the input/output interface 108. In this regard, the system may include an identification files database 218 that maintains records of patients as identified through face and/or speech recording and analytics. When the system attempts to recognize a patient through data acquired by the input/output interface 108, the system may reference the data stored in the identification files database 218. The system 100 may additionally include a log database 220 that maintains an archive of recognition data that is acquired for various patients. By way of example and not limitation, the log database 220 may store audio, video, text, and so on.

Turning now to the various processing capabilities 208 of the data processing application 202, continuing reference is made to FIG. 2. As can be seen in this figure, the data processing application 202 may utilize Text Analytics including a Natural Language Processing (NLP) module 222, which is in communication with various application services. The NLP module 222 is generally configured to process language inputs that are received as text files or in other appropriate formats. For instance, NLP module 222 may process data so that speech-to-text data is translated into structured data, medical terminology, and medical codes, e.g., CPT and ICD-10-CM/PCS codes. In this regard, the NLP module 222 may communicate with a speech-to-text service 224 and/or an optical character recognition (OCR) service 226. The speech-to-text service 224 is configured to receive audio inputs from the input/output interface 108, convert these inputs into text, and provide the text as input to the NLP module 222. The OCR service 226 is configured to receive images of text from the input/output interface 108, convert these images into computer readable text, and provide the text as input to the NLP module 222. The NLP 222 module processes these language inputs to extract certain information that is to be input into one or more of the databases 116 with which the data processing application 202 communicates. In this regard, the NLP 222 module may communicate with other services that facilitate communication between the NLP module 222 and the various databases 116. These services may include, by way of example but not limitation, a transcription service 227, a system search service 228, a system update service 229, and/or a session workflow management service 230.

The data processing application 202 may also include a person identification module 232, which is in communication with various application services. The person identification module 232 is generally configured to process face or voice recognition inputs and to correlate those inputs with medical facility records to determine or record the identity of the patient from whom the face or voice recognition inputs was derived. In this regard, the person identification module 232 may communicate with a face recognition service 234 and/or a voice recognition service 236. The face recognition service 234 is programmed with a face recognition algorithm and is configured to execute this algorithm with video inputs received from an input/output interface 108 that is associated with the audiovisual input/output device 206. The voice recognition service 236 is programed with a voice recognition algorithm and is configured to execute this algorithm with audio inputs received from an input/output interface 108 that is associated with either the audio only equipment 204 or with the audiovisual input/output device 206. The person identification module 232 receives the inputs from the face recognition service 234 and/or the voice recognition service 236 and correlates the inputs with face and voice data recorded in the identification files database 218. The person identification module 232 registers a match if one is found. If no recorded face or voice data is found to match the input, the person identification module 232 may create a new entry in the identification files database 218. The person identification module 232 may additionally communicate with other services to facilitate communication of person recognition data to other parts of the system. These services may include, by way of example and not limitation, the transcription service 227, the system search service 228, the system update service 229, and/or the session workflow management service 230.

Figure 4A:
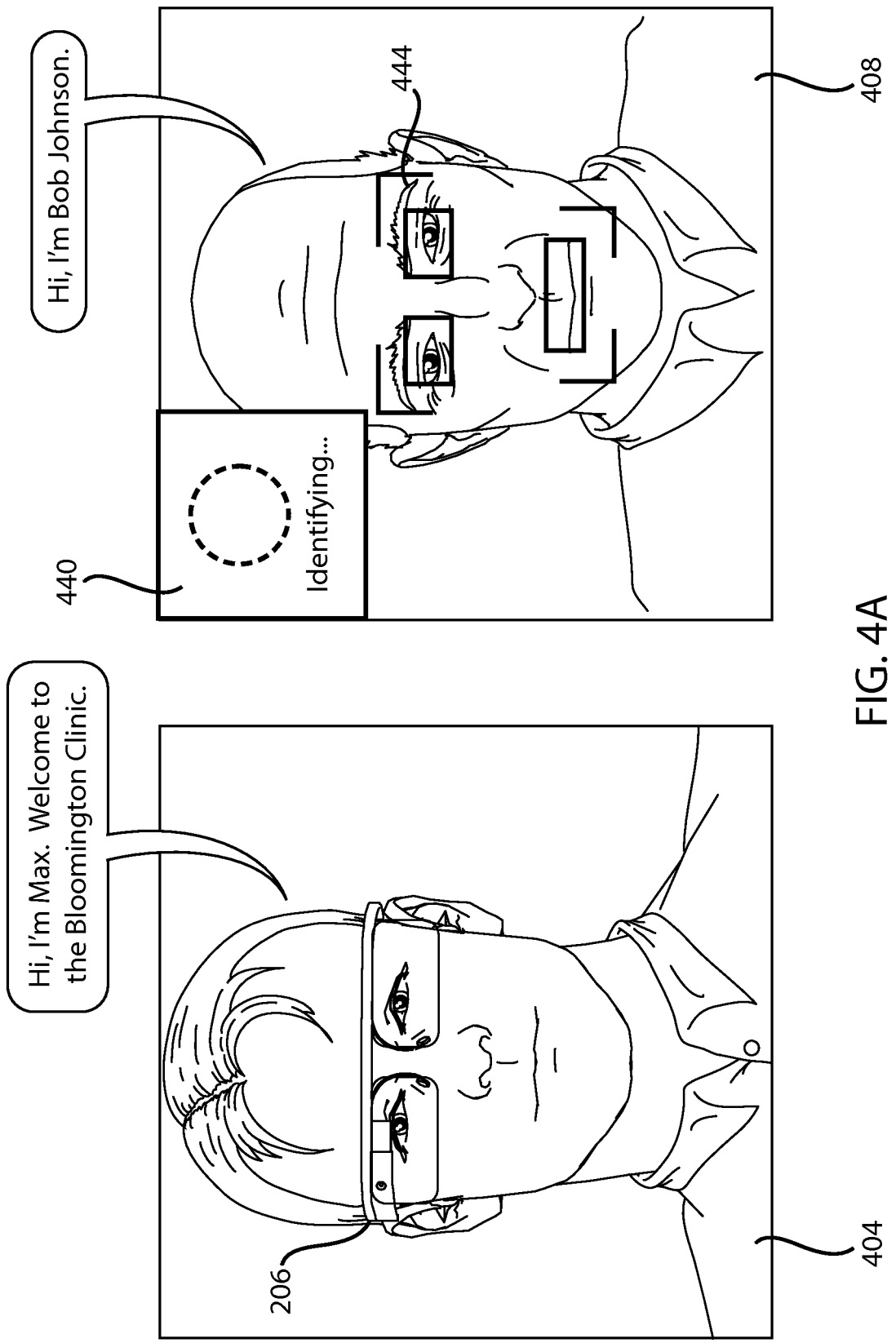
Figure 4B:
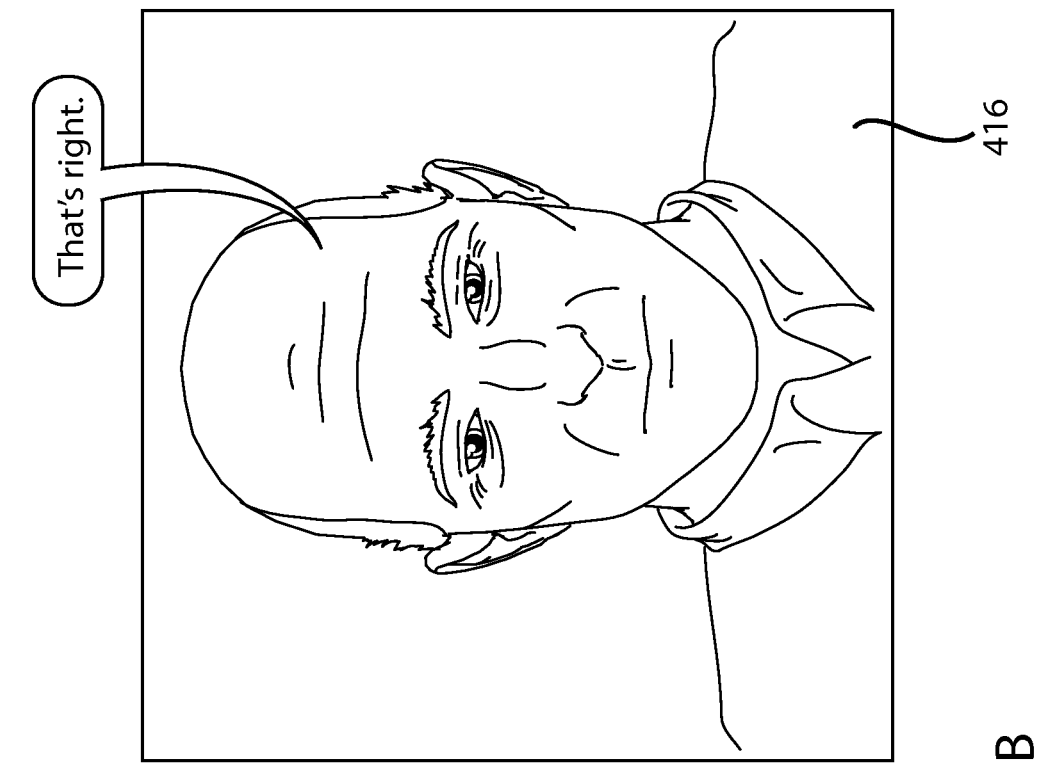
Figure 4B:
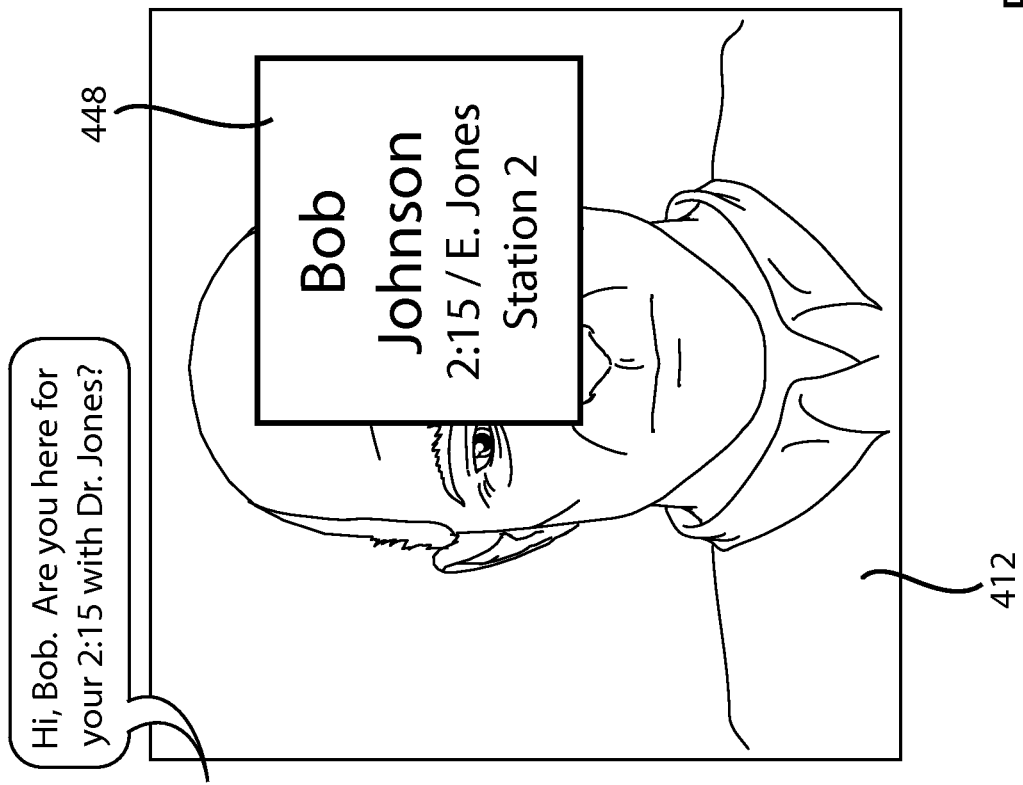
Figure 4C:
Figure 4C:
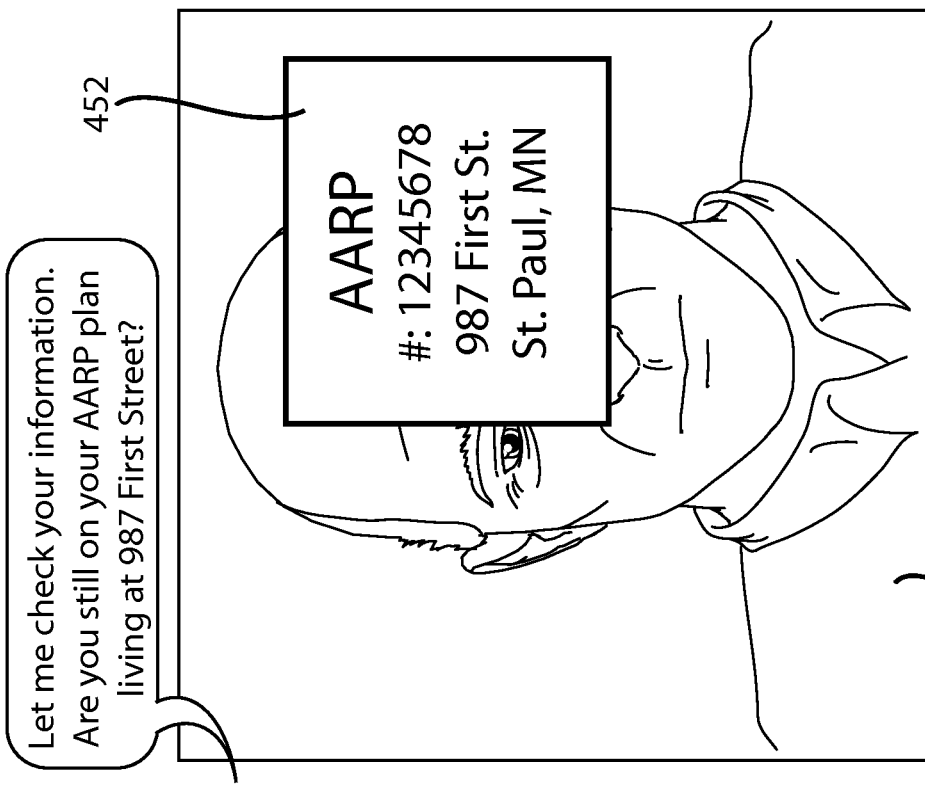
Figure 4D:
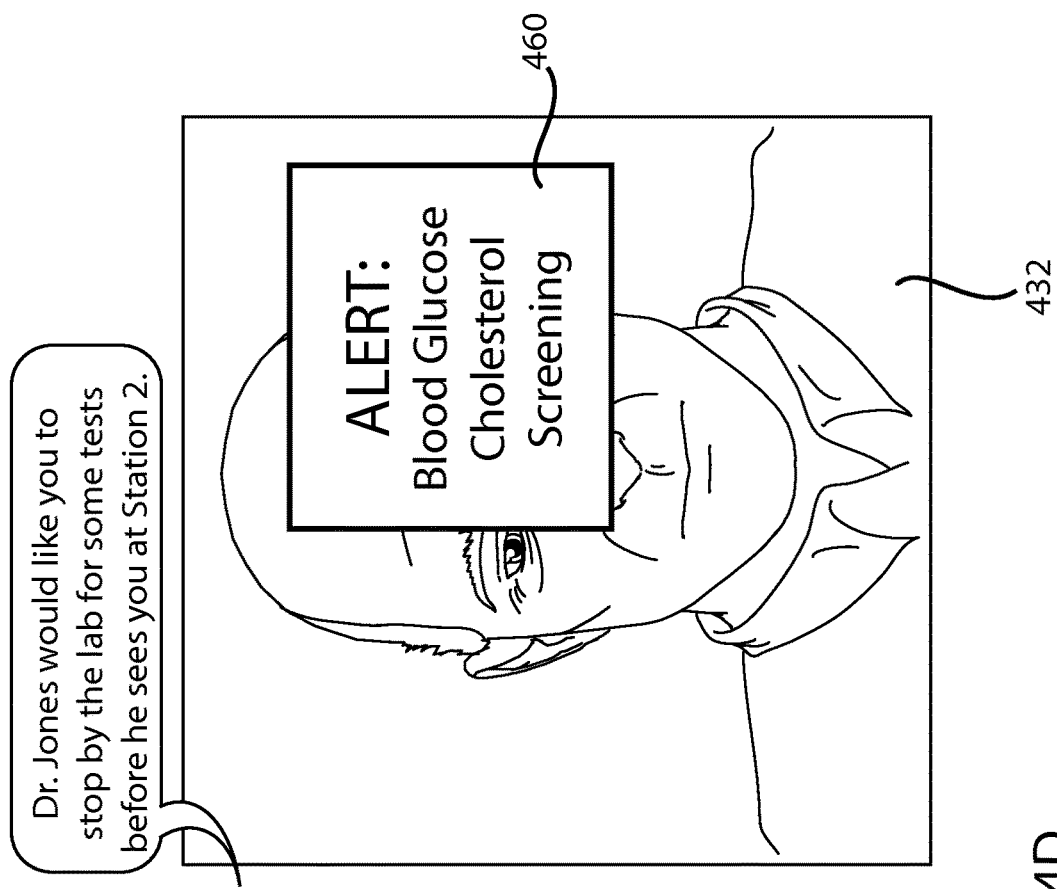
Figure 4D:
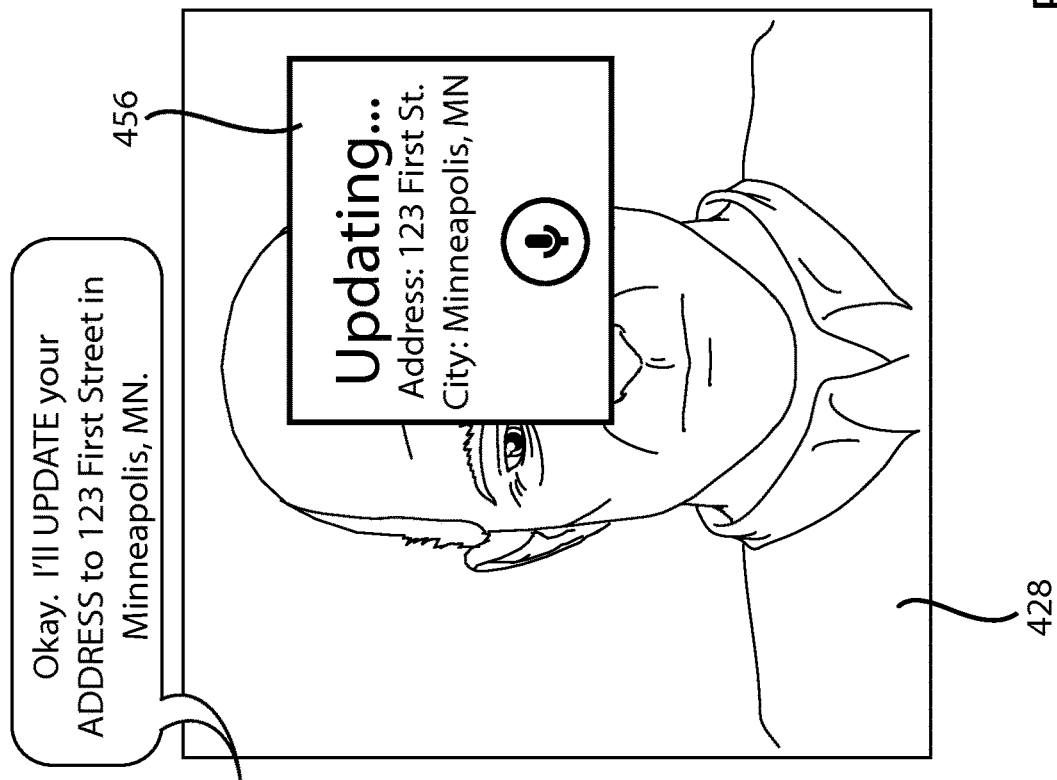

In certain embodiments, the devices 204, 206 may be implemented as a wearable computing device. For example the input/output devices 204, 206 may be implemented as a headset or the like and may be may be worn by a user on his or her head or face. For example, the device 204, 206 may be configured to be worn on a user's head (see, e.g., FIG. 4A). For example, device 206 may further include a user-visible screen for displaying information. The screen may be worn in such a way that the user can substantially maintain line-of-sight interaction with another person while using the screen. For instance, the user may face the other person and glance at the screen without the user's head turning or the user facing away from the other person.

The devices 204, 206 may include various sensors, including but not limited to gesture recognition sensors, eye tracking, gaze tracking, touch sensors (e.g. a touch screen or touch pad), and other sensors to facilitate receiving of input by the device 204, 206. The devices 204, 206 may also contain sensors capable of determining who is using the device 204, 206 and whether the user is authorized to access particular information.

Data Entry and Workflow Method

Figure 3:
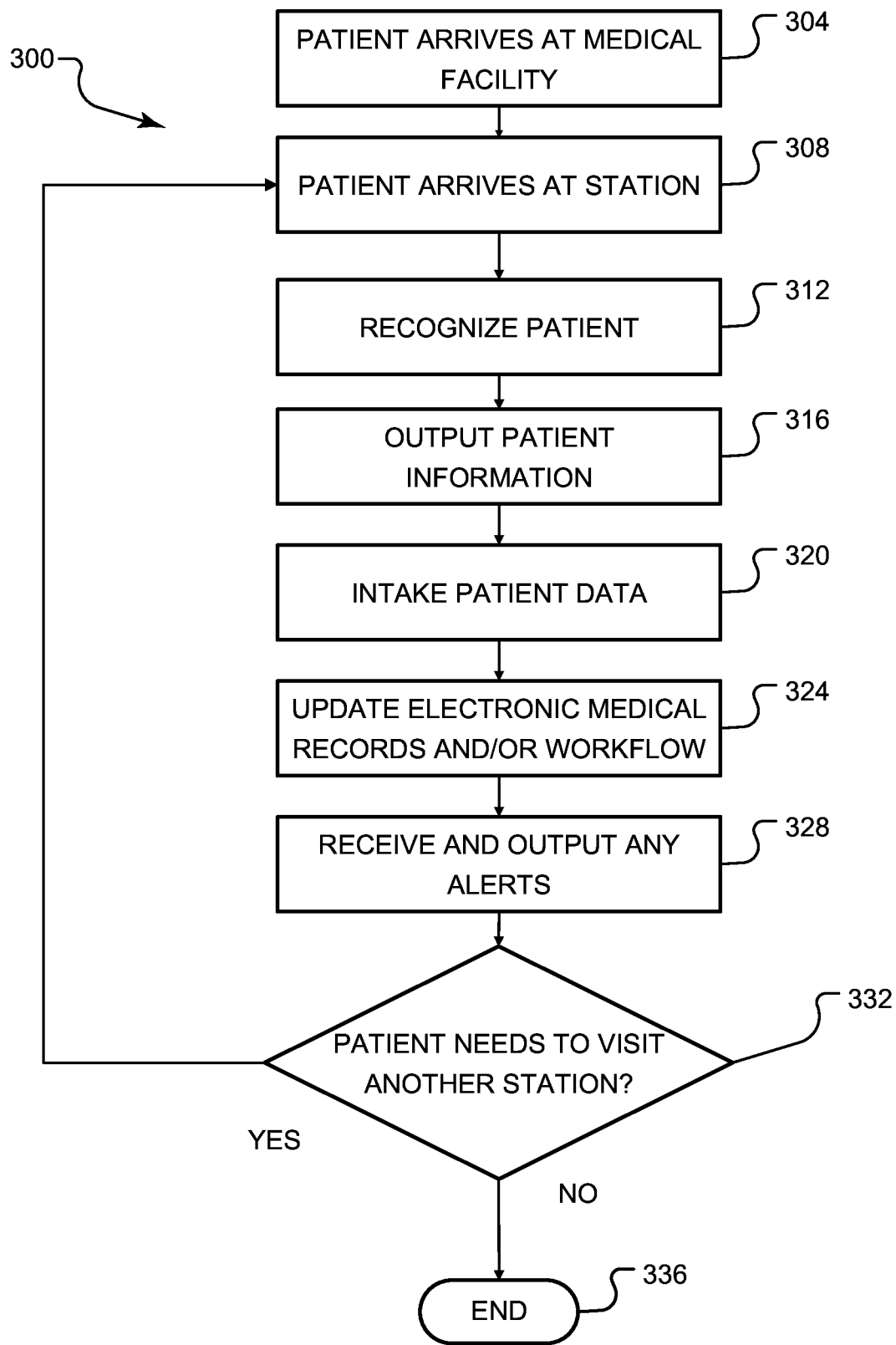
FIG. 3 is a flow chart that illustrates a method in accordance with embodiments discussed herein.

FIG. 3 is a flow chart 300 that illustrates a method in accordance with embodiments discussed herein. The method 300 may include using a data processing application 202 that is a component of a system 100 that provides integrated data entry and workflow capabilities in a hospital, medical facility, or the like. Typically, a medical or other facility that utilizes the system 100 may include a number of stations. By way of example and not limitation, stations included within the facility may include an admitting station, a lab station, a vitals station, and/or a doctor's station. The following description of the method 300 will refer to these example stations; however, it should be appreciated that the method 300 may be used in connection with other stations not specifically mentioned. It should also be appreciated that the order in which the following operations are described is by way of example and not limitation. The various operations may occur in any order, some operations may be omitted, and some operations may be repeated as appropriate depending on the particular implementation and depending on the need for particular operations that may arise as data is entered or output.

Initially, in box 304, the patient arrives at the medical facility. Typically, the patient will visit a number of stations during his or her visit to the medical facility. However, the patient more than likely will first visit an admitting station. Thus, after the patient arrives at the patient medical facility in box 304, the patient goes directly to the admitting station.

In box 308, the patient arrives at a particular station, in this case the admitting station. Here, the patient is greeted by medical personnel who in accordance with embodiments discussed herein are equipped with a computing device 100 that includes an input/output interface 108. The input/output interface 108 is associated with either an audio-only input/output device 204 or an audiovisual input/output device 206.

In box 312, the system 100 recognizes the patient. Specifically, audio and/or visual data may be acquired through the operation of the input/output interface 108 and passed from the computing device 104 to the person identification module 232, which operates to recognize the patient. In this regard, the person identification module 323 may utilize the face recognition service 234 and/or the voice recognition service 236, which processes the raw data and provides input to the person identification module 232. The person identification module 232 may then compare this input with identification data contained in the identification files database 218. If, in box 332, the patient is at the admitting station and is being initially recognized by the system 100 the person identification module 232 may perform an initial search of the identification files database 218. If a match is found, the person identification module 232 may register that the patient is present at the medical facility and transfer this information to other parts of the system 100. If no recorded face or voice data is found to match the input, the person recognition module 232 may create a new entry in the identification files database 218 and transfer this information to other parts of the system 100. Because the system 100 now registers that the patient is present at the medical facility either through a recalled identification file or a newly created identification file, the full process of recalling and/or creating need not be done when the patient arrives at other stations within the facility due to caching of this information in the workflow or other processes.

In box 316, the system 100 provides medical personnel with information regarding the patient. Specifically, the system 100 may communicate patient information to medical personnel through audio and/or visual output provided through the operation of the input/output interface 108. Here, the input/output interface 108 may output patient information to the medical personnel who is wearing or otherwise using a headset or the like associated with the computing device 104. In the event that the input/output interface 108 is associated with an audio-only input/output device 204, medical personnel may receive audio outputs such as recordings from a microphone associated with the headset. In the event that the input/output interface 108 is associated with an audiovisual input/output device 206, medical personnel may receive audio outputs from a headset microphone and/or visual data displayed on a visual display device within the headset. In box 316, the computing device 104 may output patient data or information such as medical records that are called-up by the system 100 once the patient has been recognized and registered as being present within the medical facility. For example, in box 316, the computing device 104 may output a patient's name, address, insurance information, and so on.

In box 320, the system 100 intakes patient data. Specifically, medical personnel may speak voice inputs or commands into their headset microphone and these inputs may then be transferred to the system 100 through the input/output interface 108. For instance, if the patient is located at the admitting station, box 320 may include in-taking patient data such as new address, new insurance information, the reason for the patients visit to the medical facility, and so on.

In box 324, the system 100 may update electronic medical records and/or workflow tickets. For example, if the patient is at the admitting station, the system 100 may update medical records with new address or insurance information, if any, provided by the patient. Here, the NLP module 222 may recognize certain keywords or commands spoken by medical personnel and picked-up by their headset microphone. These keywords or commands may be spoken prior to information that needs to be recognized and recorded in an appropriate location. For example, medical personnel may speak one or more keywords such as "update," "your medical records," "new address," and so on. Following these keywords, medical personnel may then repeat the information first spoken by the patient and in so doing speak the information that needs to be recognized and recorded into the headset microphone. The NLP module 222 may be configured to recognize such commands and acquire the data from the voice stream and record the appropriate data in a medical record. In this regard, the NLP module 222 may utilize the speech-to-text service 224. In addition to updating medical records, the system 100 may also generate or update workflow tickets. For example, if the patient is at the admitting station and has given a reason for his or her visit to the medical facility, medical personnel may enter appropriate voice commands through the headset microphone to generate a workflow ticket that is received by other stations within the medical facility.

In box 316, the system 100 generates one or more alerts and provides these alerts to medical personnel through the computing device 104. The alerts may be stored in the provider alerts database 216 for delivery to medical personnel at an appropriate time. For example, the system 100 may provide medical personnel with an alert informing them that they must tell the patient with whom they are talking that the patient is in need of a particular test. The system 100 may communicate the alert to medical personnel through audio and/or visual output provided through the operation of the input/output interface 108. Here, the input/output interface 108 may output the alert to the medical personnel who is wearing or otherwise using a headset or the like associated with the computing device 104. In the event that the input/output interface 108 is associated with an audio-only input/output device 204, medical personnel may receive audio outputs such as recordings from a microphone associated with the headset. In the event that the input/output interface 108 is associated with an audiovisual input/output device 206, medical personnel may receive audio outputs from a headset microphone and/or visual data displayed on a visual display device within the headset.

In decision box 332, a determination is made if the patient needs to visit another station. For example, if the patient has just arrived at the medical facility and is at the admitting station he or she will most likely next visit a lab or vital station prior to later visiting a doctor station. If the patient is to be treated or otherwise cared for at another station, box 308 follows after box 332. In this regard, one or more of the various operations embodied in boxes 312 and 328 may take place at the next station. If the patient no longer needs to visit an additional station, the method may end at box 336.

Examples

FIGS. 4A through 4E illustrate an example interaction between medical personnel and a patient. The specific interaction illustrated in FIGS. 4A through 4E is one that takes place at an admitting station and involves a receptionist and a patient who has just arrived at the medical facility.

Panel 404 shows a receptionist who is wearing an audiovisual input/output device 206 configured as a headset that includes a microphone, a speaker, a camera, and a visual display device on the inside of an eye display. As shown in panel 404, the receptionist greets the patient who is shown in panel 408.

Panel 408 is a view of the patient from the perspective of the receptionist. Panel 408 includes certain visual output that is provided to the receptionist on the inside of the receptionist's display. Specifically, the panel 408 includes an icon 440 which indicates that the system is in the process of visually identifying the patient who concurrently is interacting with the receptionist. Panel 408 additionally includes visual indicia 444 of the face recognition process which appear overlaid on the face of the patient.

Panel 412 shows additional information 448 that is displayed to the receptionist as the receptionist continues to interact with the patient. Here, the receptionist is provided with information regarding the patient that has been brought-up through the operation of the system 100. Specifically, the system 100 has recognized the patient through facial recognition, correlated the patient with his or her records, and delivered those records, or a portion of those records, to the receptionist through the visual display associated with the receptionist's headset. This occurs concurrently as the receptionist continues to interact with the patient.

Panel 416 shows that the conversation continues between the receptionist and the patient. Specifically, the patient responds to a question asked by the receptionist.

Panel 420 shows additional information 452 that is displayed to the receptionist through the output device associated with his headset. Specifically, the system 100 provides the receptionist with the patient's insurance information through a display of this information that appears on a display of the audiovisual input/output device 206. Concurrently, the receptionist asks the patient to verify whether or not the information, including insurance and address information, is correct.

Panel 424 shows that the conversation continues between the receptionist and the patient. Specifically, the patient indicates that the address information on file at the medical facility is out of date.

Panel 428 shows that the receptionist indicates to the patient that he will update the patient's medical records so that they are current. In so doing, the receptionist speaks a command into the headset microphone that is then processed by the system 100. As shown in panel 428, the display device associated with the audiovisual input/output device 206 (e.g., headset) may display an icon 456 or other indication that the command is being executed by the system 100.

Panel 432 shows that the conversation between the receptionist and patient continues. Here, the receptionist informs the patient that the doctor wishes the patient to stop by a lab station before he comes to see the doctor. As can be seen in panel 432, the receptionist becomes aware of this information though an alert 460 displayed on the headset display screen. Specifically, the display of the audiovisual input/output device 206 displays an alert stating that a blood glucose and cholesterol screening is required.

Panel 436 show that the interaction between the receptionist and the patient ends with the patient thanking the receptionist. Throughout the interaction illustrated in FIGS. 4A through 4E, the medical records were updated, the patient was identified as being present within the medical facility, and the patient was given information as to his next stop, all while the receptionist and the patient were able to maintain eye contact.

Figure 5A:
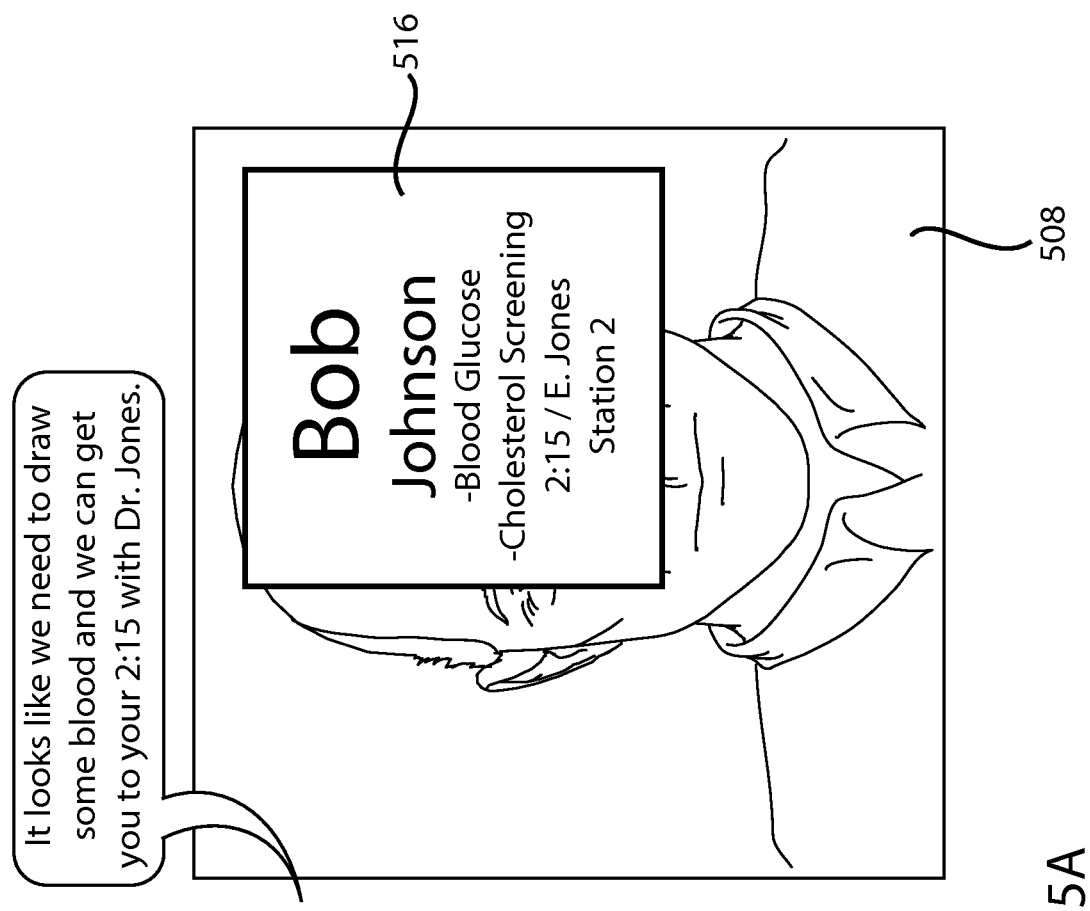
FIGS. 5A through 5B illustrate another interaction between the patient and medical personnel.
Figure 5A:
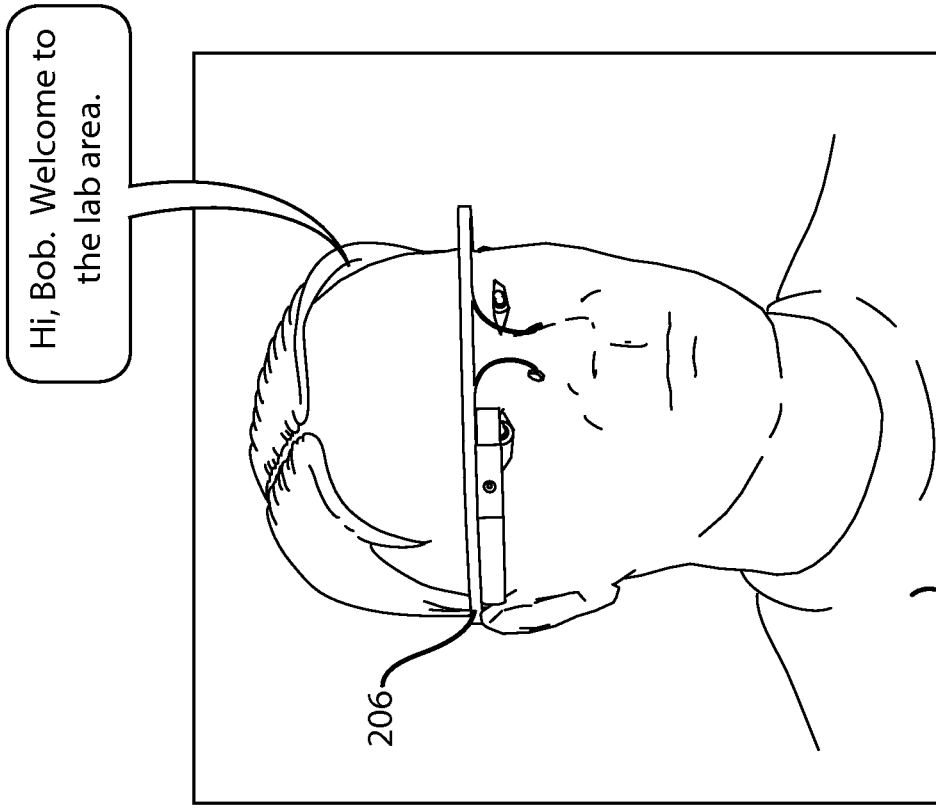
Figure 5B:
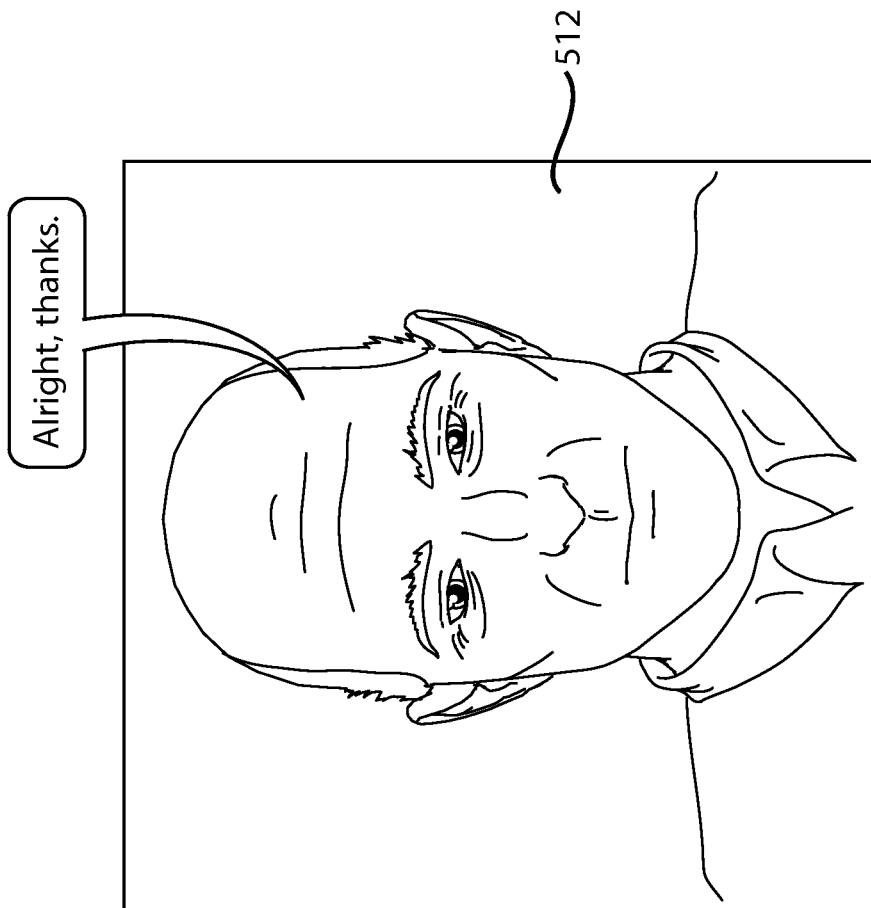

FIGS. 5A through 5B illustrate another interaction between the patient and medical personnel. The specific interaction illustrated in FIGS. 5A through 5B is one that takes place at lab station and involves a lab technician and the patient who has just come from the admitting station.

Panel 504 shows that the lab technician greets the patient as the patient enters the lab station. As can be seen in panel 504, the lab technician is equipped with the audiovisual input/output device 206 configured with a speaker, microphone, camera, and display device.

Panel 508 shows that the conversation between the lab technician and the patient continues. Specifically, the lab technician indicates that the doctor has ordered that a blood sample be taken prior to the patient visiting with the doctor. The lab technician is aware of this information and of the patient's identity through a message 516 displayed on the display device associated with his audiovisual input/output device 206. As can be seen in panel 508, this display includes the patient's name and the work required to be performed by the technician.

Panel 512 shows that the technician's work is complete and the interaction between the technician and the patient ends with the patient thanking the technician. Throughout the interaction illustrated in FIGS. 5A and 5B, the technician was provided with patient information and performed required tests, all while the technician and the patient were able to maintain eye contact.

Figure 6A:
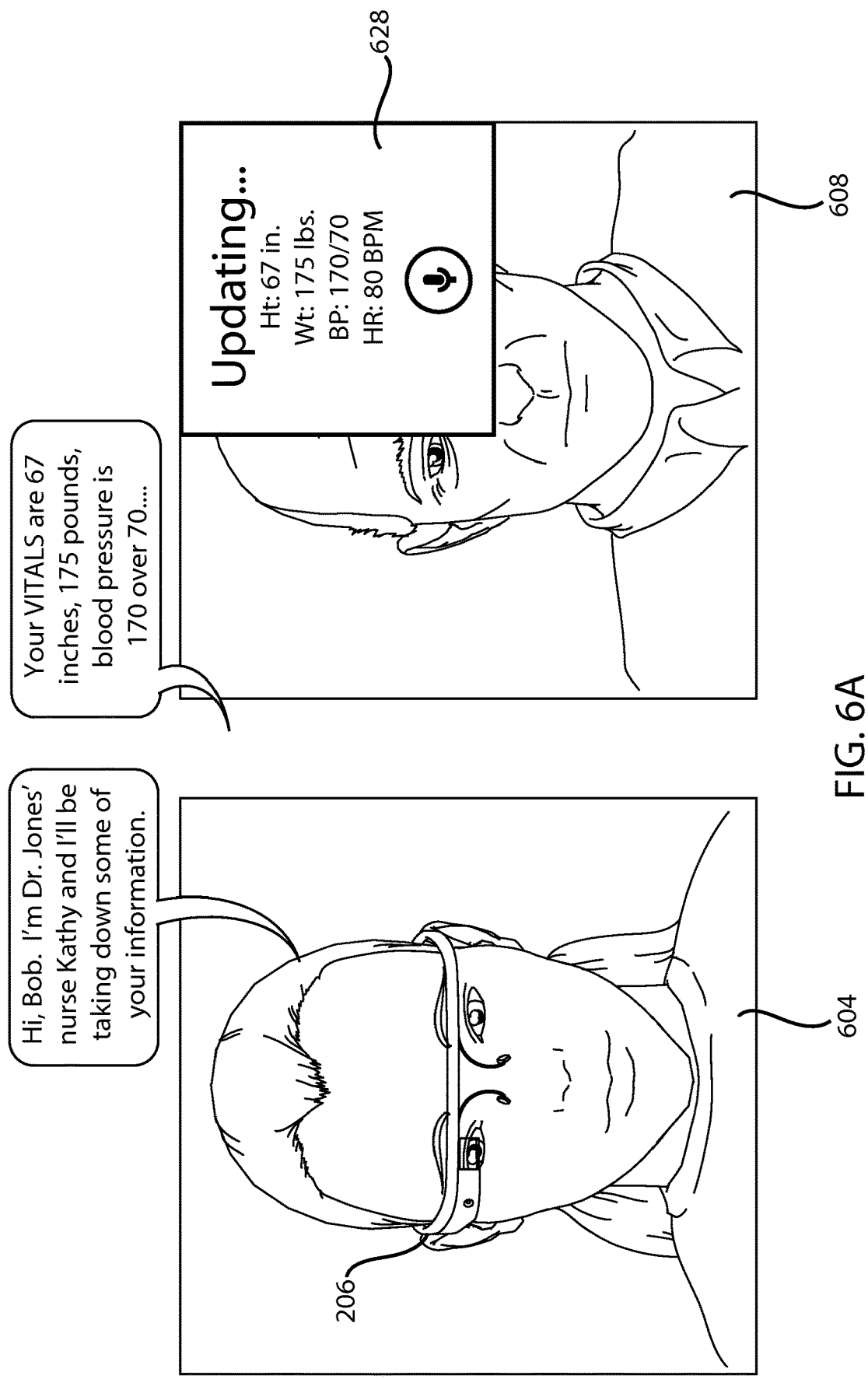
FIGS. 6A through 6C illustrate another interaction between the patient and medical personnel.
Figure 6B:
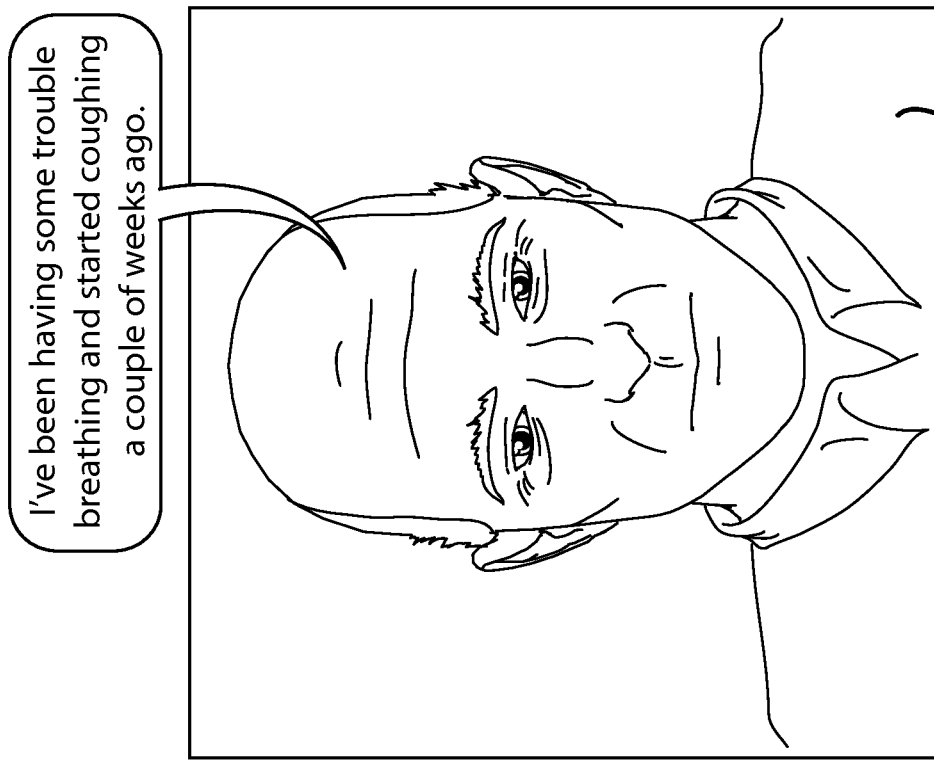
Figure 6B:
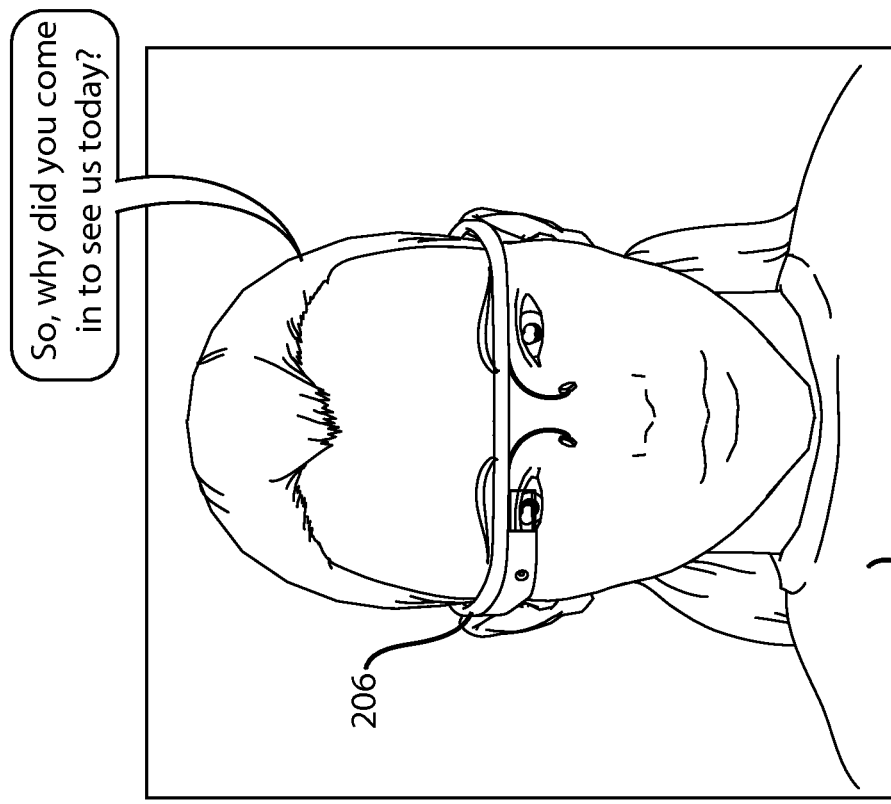
Figure 6C:
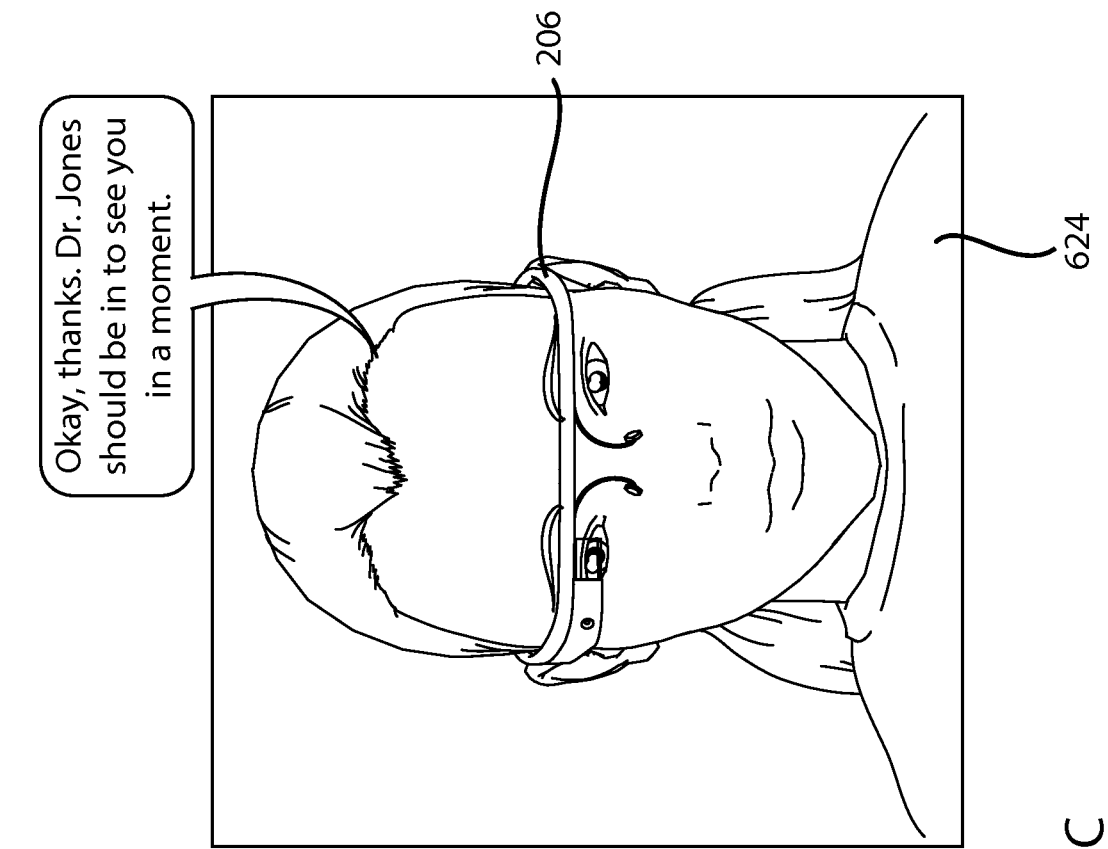
Figure 6C:
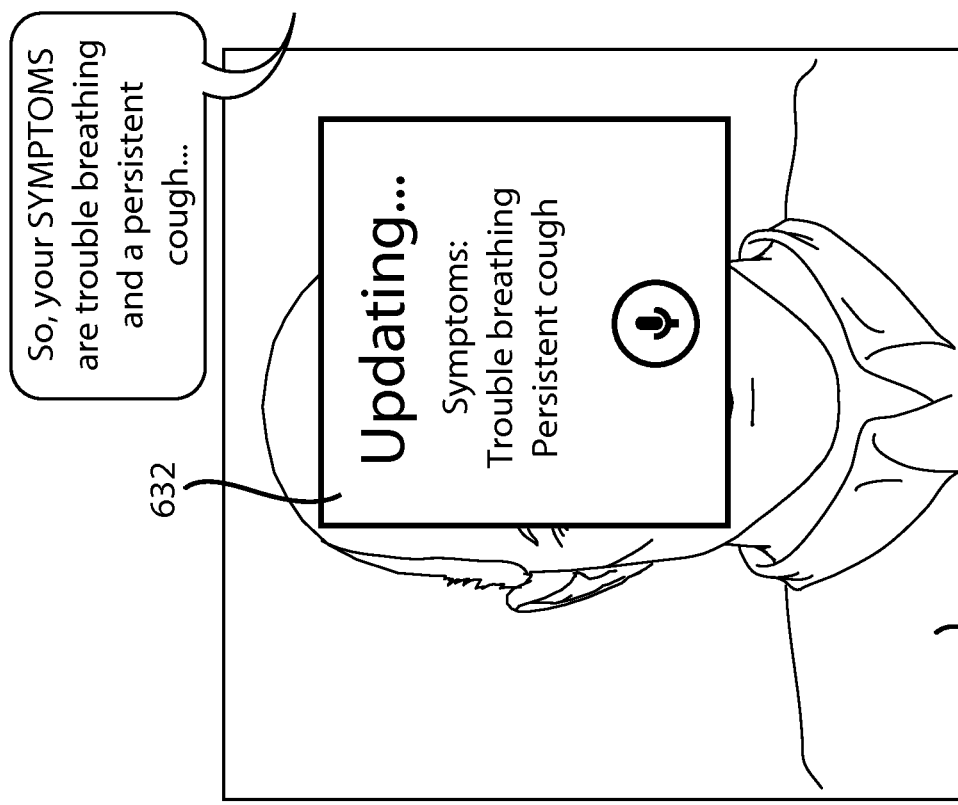
Figure 7A:
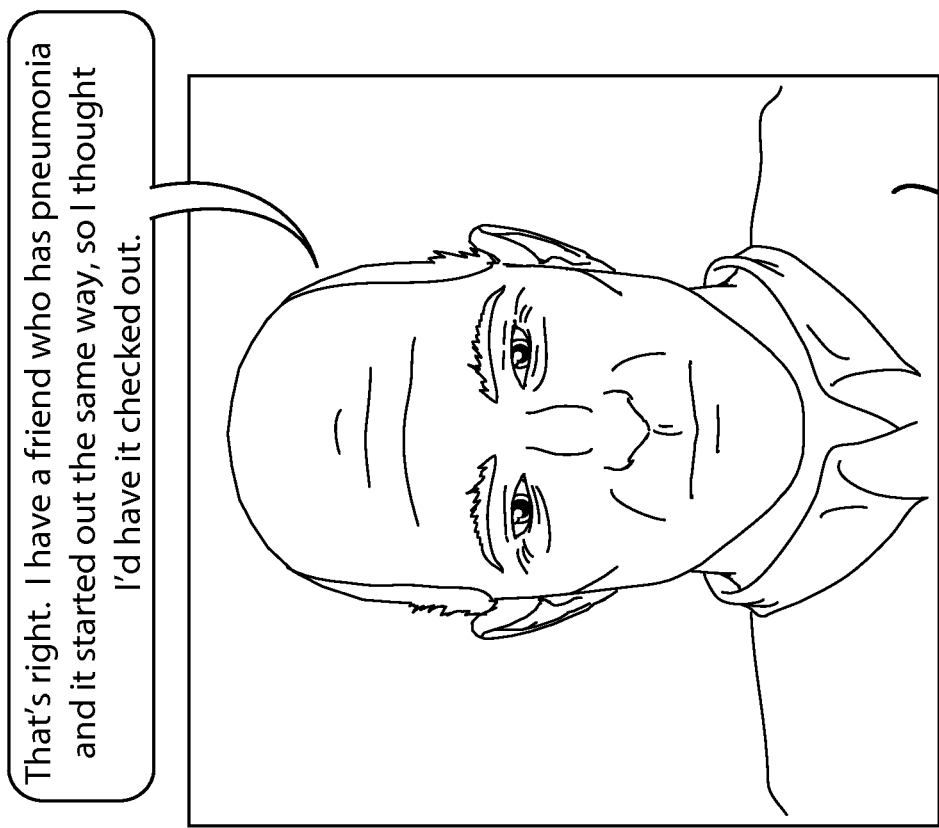
Figure 7A:
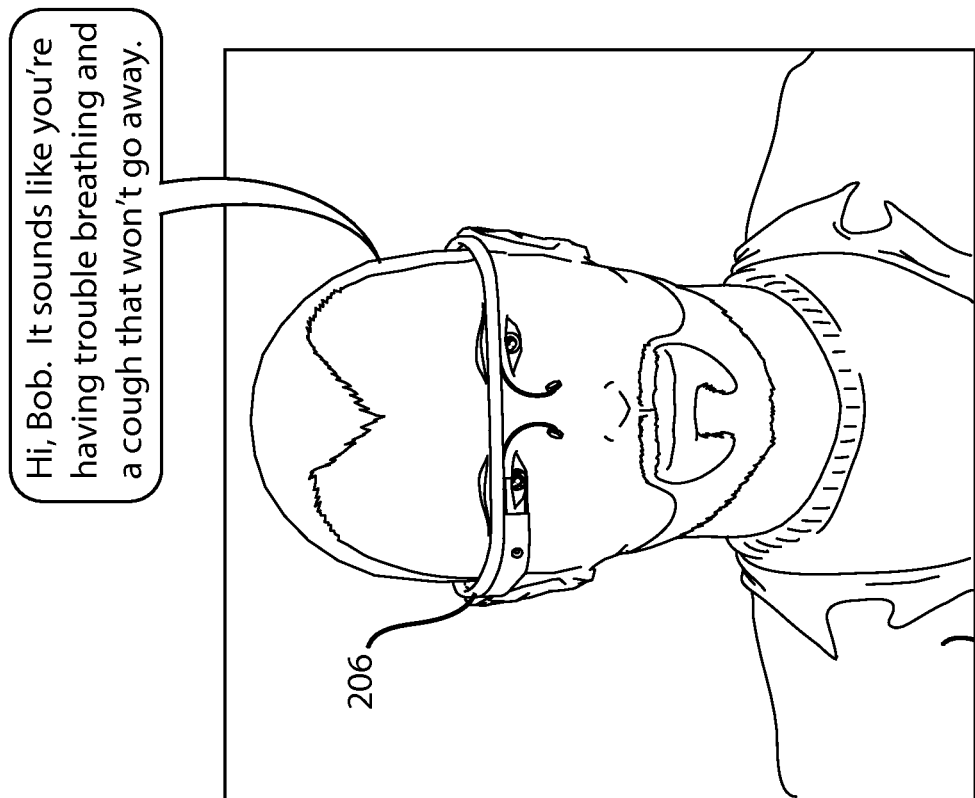
Figure 7B:
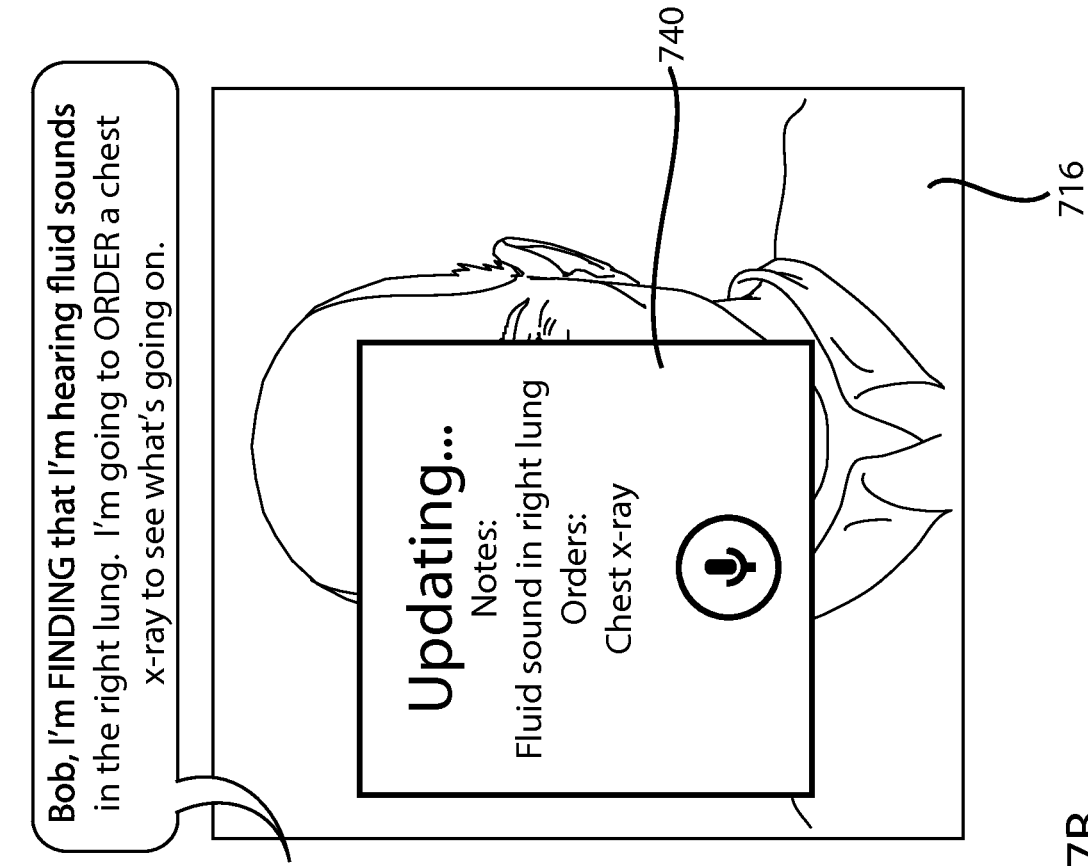
Figure 7B:
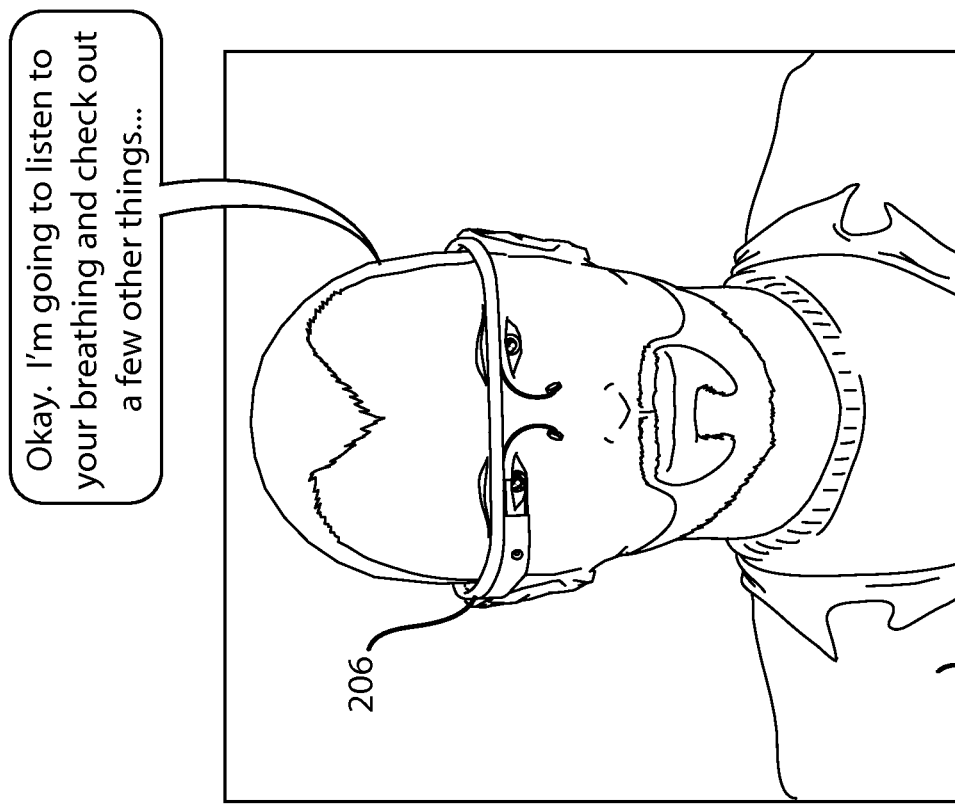
Figure 7C:
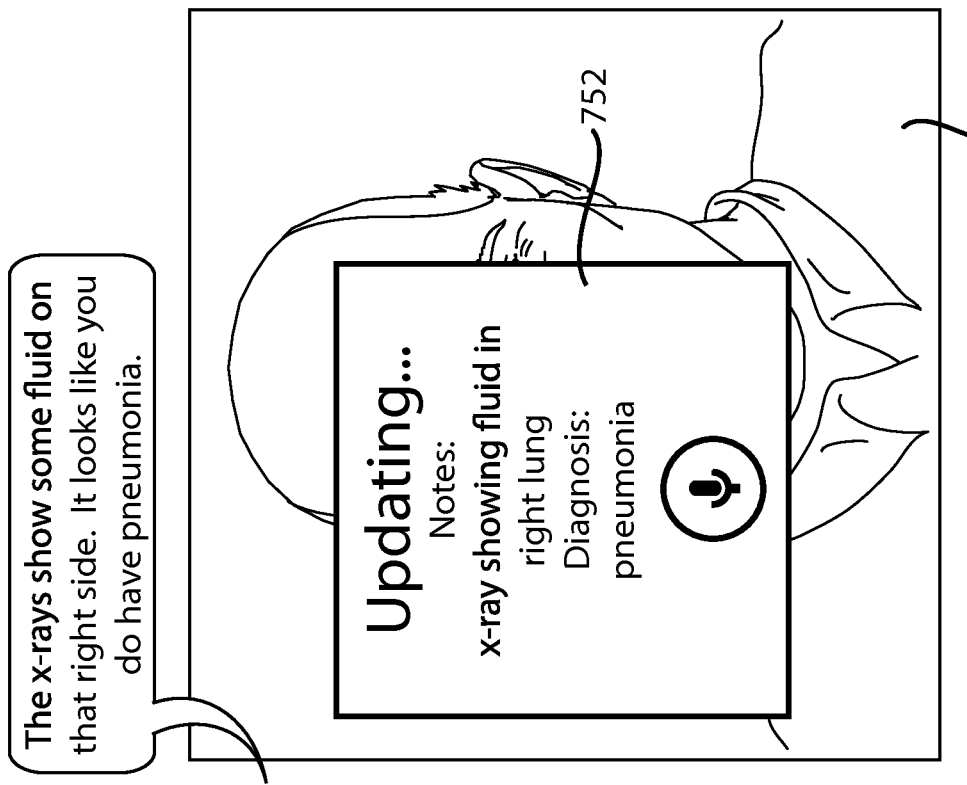
Figure 7C:
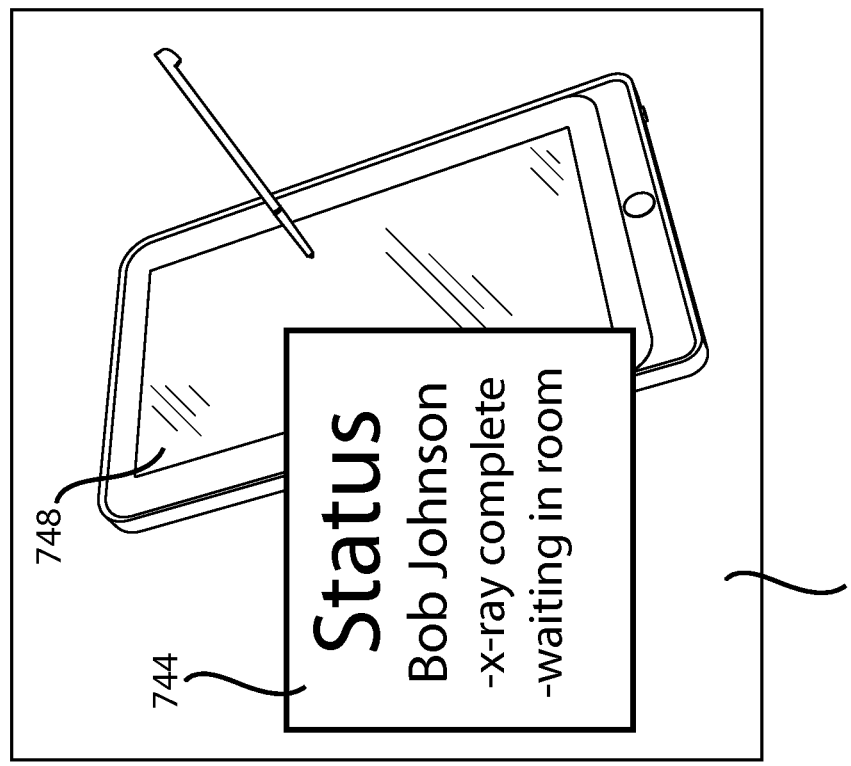
Figure 7D:
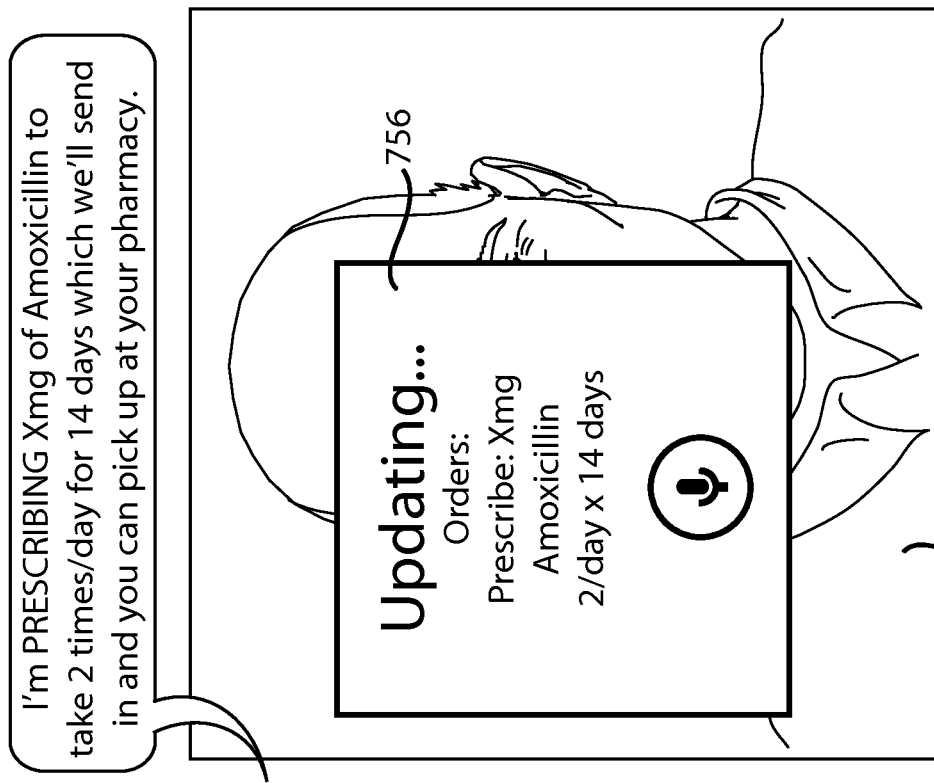
Figure 7D:
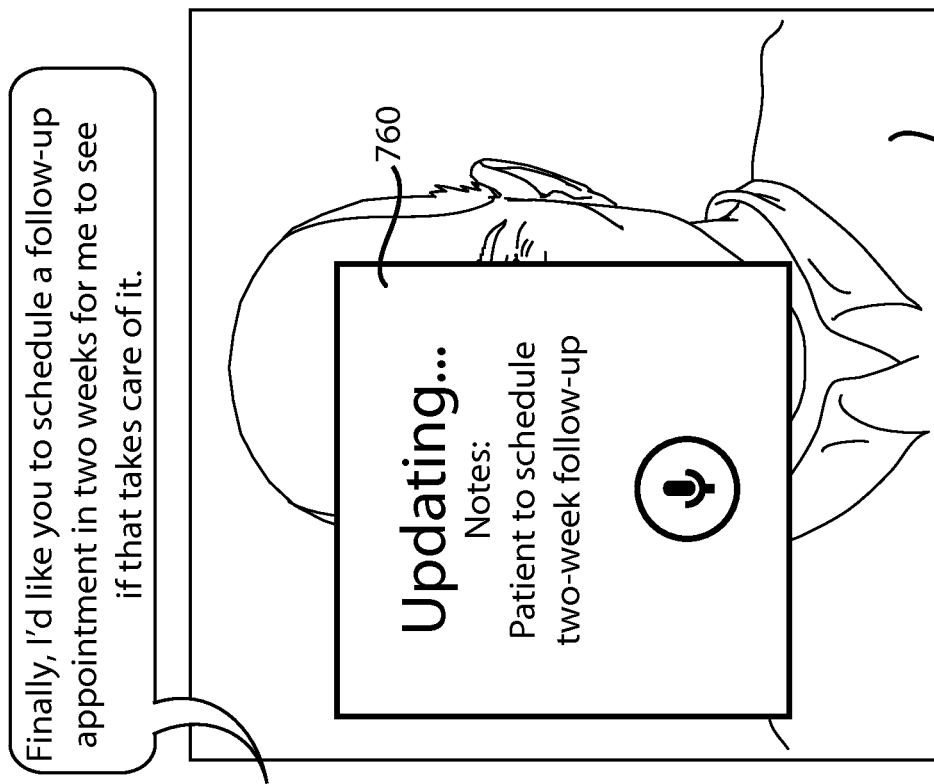

FIGS. 6A through 6C illustrate another interaction between the patient and medical personnel. The specific interaction illustrated in FIGS. 6A through 6C is one that takes place at nurse station and involves a nurse and the patient who has just come from the lab station.

Panel 604 shows that the nurse initially greets the patient as the patient arrives at the nurse station. As can be seen in panel 604, the nurse is equipped with an audiovisual input/output device 206 that includes a speaker, microphone, camera, and display device.

Panel 608 shows that the conversation between the nurse and the patient continues as the nurse takes the patient's vitals. Specifically, the nurse measures the patient's vitals and speaks the information she acquires out loud and into her headset microphone. In so doing, the information is entered into the system 100 and an indication of this entry is displayed to the nurse through an icon 628 or other menu item displayed on her headset display device. As can be seen in panel 608, this icon includes an updating message along with a text indication of the vitals that she has just acquired from the patient.

Panel 612 shows that the conversation between the nurse and the patient continues. Specifically, the nurse asks the patient for his reasons for coming to the medical facility that day.

Panel 616 shows that the conversation between the nurse and the patient continues. Specifically, the patient responds to the nurse by reporting symptoms such as trouble breathing and coughing.

Panel 620 shows that the conversation between the patient and the nurse continues with the nurse repeating the symptoms reported by the patient in connection with a trigger word recognized by the system 100. Specifically, the nurse says "your symptoms are trouble breathing and persistent cough." The system 100 recognizes this as a voice command that indicates that medical records need to be updated with this information. Thus, as can be seen in panel 620, the nurse is provided with an indication on her headset display device that these symptoms are being recorded. Specifically, text is displayed through an icon 632 that contains a message such as "updating symptoms: trouble breathing, persistent cough."

Panel 624 shows that the conversation between the nurse and the patient continues with the nurse saying thank you to the patient and indicating that the doctor will be with him in a moment. Throughout the interaction illustrated in FIGS. 5A and 5B, the nurse takes the patient's vitals and enters the patient's vitals into the system, all while the nurse and the patient were able to maintain eye contact.

FIGS. 7A through 7E illustrate another interaction between the patient and medical personnel. The specific interaction illustrated in FIGS. 7A through 7E is one that takes place at a doctor station and involves a doctor and the patient who has just come from the nurse station.

Panel 704 shows that the doctor initially greets the patient as the patient arrives at the doctor station. As can be seen in panel 704, the doctor is equipped with an audiovisual input/output device 206 that includes a speaker, microphone, camera, and display device. As can be seen in panel 704, the doctor repeats symptoms which the patient had previously reported to the nurse. The system 100 may provide the doctor with this information through the display device or the audio device associated with the doctor's headset.

Panel 708 shows that the conversation between the doctor and the patient continues. Specifically, the patient responds to the doctor by confirming what the doctor has said and providing additional information.

Panel 712 shows that the conversation between the doctor and the patient continues. Specifically, the doctor states the next steps that he would like to take.

Panel 716 shows that the conversation between the doctor and the patient continues with doctor stating that he has found fluid in the patient's chest and that he will order an additional test. In so doing, the doctor speaks commands into his headset microphone which are recognized by the system 100. In response to receiving the commands, the system 100 then updates medical records and/or workflow items as indicated by the visual output 740 seen by the doctor in panel 716.

Panel 720 shows that the doctor receives certain status information 744 on a tablet computer 748. Here, the tablet computer 748 may be used to supplement the information entered through the doctor's audiovisual input/output device 206. As shown in panel 720, the status information 744 indicates that the tests the doctor ordered are complete and the patient is located in a particular waiting room.

Panel 724 shows that the meeting between the doctor and the patient has resumed. The doctor states that additional tests have confirmed his initial findings and that the doctor's diagnosis is confirmed. As this information is conveyed to the patient, the doctor speaks the information into his audiovisual input/output device 206 microphone so that this information is recognized and processed by the system 100. In response, the system 100 updates medical records and/or workflow items as indicated by the visual output 752 seen by the doctor in panel 724.

Panel 728 shows that the conversation between the doctor and the patient continues with the doctor stating that he will prescribe a particular medication. As this information is conveyed to the patient, the doctor speaks the information into his audiovisual input/output device 206 microphone so that this information is recognized and processed by the system 100. In response, the system 100 updates medical records and/or workflow items as indicated by the visual output 756 seen by the doctor in panel 728.

Panel 732 shows that the conversation between the doctor and the patient continues with the doctor stating that he needs to schedule a follow-up appointment. As this information is conveyed to the patient, the doctor speaks the information into his audiovisual input/output device 206 microphone so that this information is recognized and processed by the system 100. In response, the system 100 updates medical records and/or workflow items as indicated by the visual output 760 seen by the doctor in panel 732.

Panel 736 shows that the doctor's work is complete and the interaction between the patient and the doctor ends with the patient thanking the doctor. Throughout the interaction illustrated in FIGS. 7A and 7E, the doctor performs various tests, updates medical records, prescribes medications, and schedules follow-up appointments, all while the doctor and the patient were able to maintain eye contact.

Figure 8B:
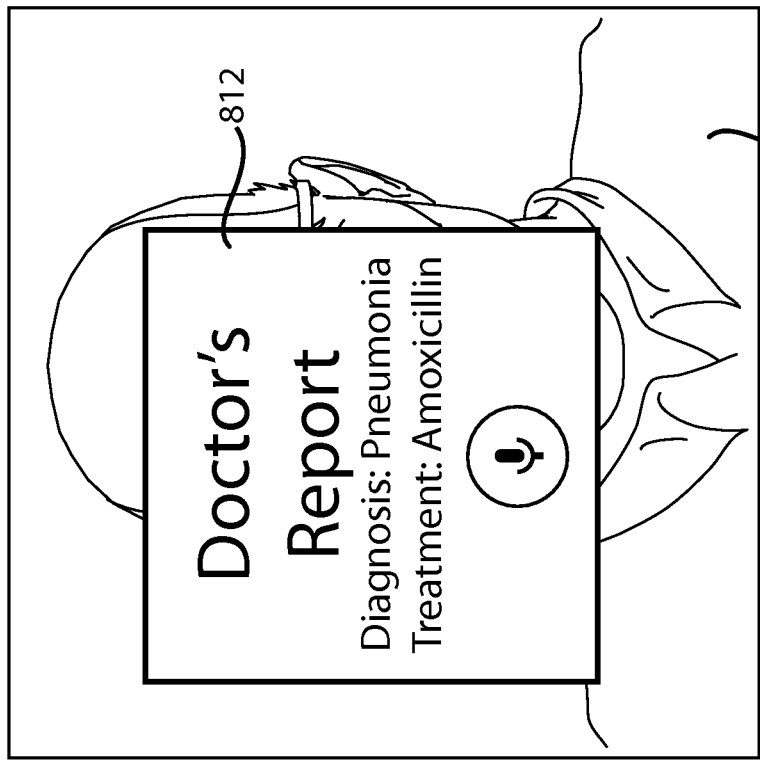
FIGS. 8A through 8C illustrate another interaction between the patient and medical personnel.
Figure 8A:
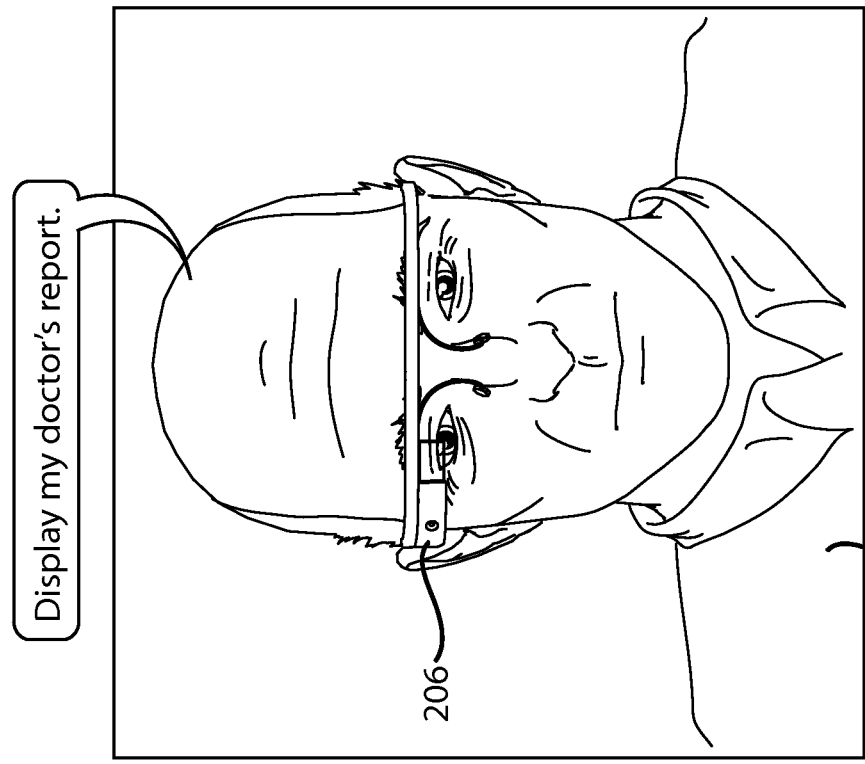
Figure 8C:
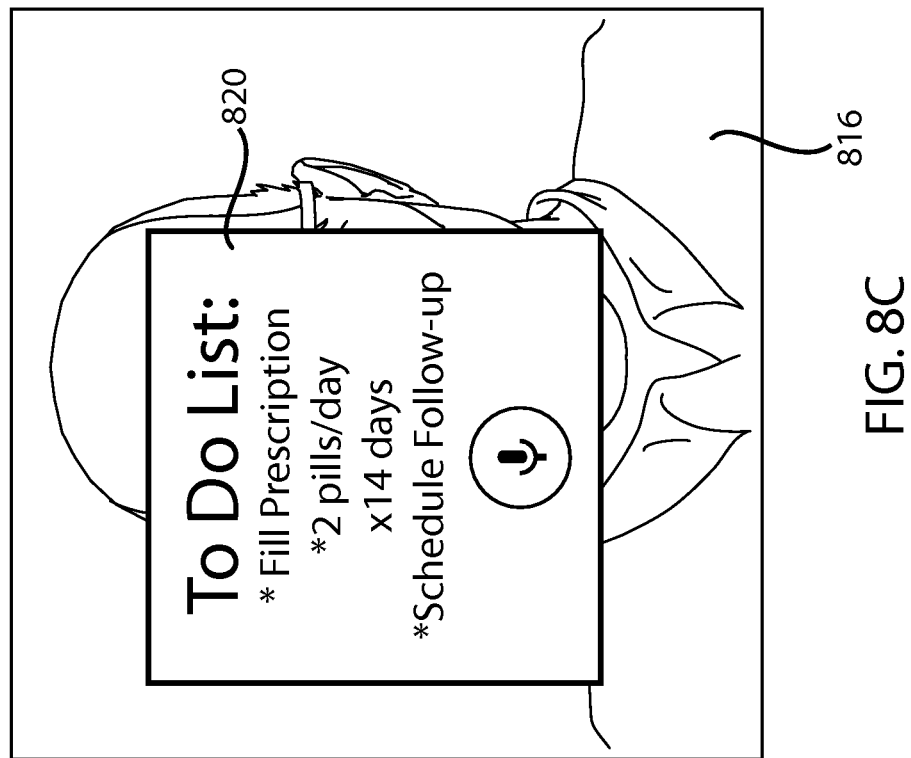

FIGS. 8A through 8C illustrate another use for the audiovisual input/output device 206 in which the patient uses the device to review their medical information. As mentioned above, the healthcare database 212 may include information to share content such as prevention, monitoring, and self-care of conditions or symptoms directly with patients using a patient version of the device to enhance patient education in a private, secure manner. FIGS. 8A through 8C illustrate this interaction between the patient and the healthcare database 212.

Panel 804 shows the patient using an audiovisual input/output device 206 that includes a speaker, microphone, camera, and display device. The audiovisual device 206 may be the patient's own device or may be a device lent to the patient by the medical facility for the purpose of watching or hearing privately, video or audio content related to his or her condition or reviewing his or her medical records. Depending on the implementation, the patient may use the device in the privacy of their own home or room with the medical facility. As shown in panel 804, the patient may begin a medical record review session by speaking a voice command into a microphone associated with the headset. The system 100 recognizes this voice command and responds by initiating a session with the healthcare database 212.

Panel 808 shows that the patient's use of the audiovisual device 206 to access the healthcare database 212 to view his medical records continues. As shown in panel 808, the system 100 responds to the patient's request by outputting information on the display device associated with his audiovisual device 206. Specifically, the system outputs a doctor's report 812 or a portion thereof that indicates a diagnosis and a prescribed treatment from the patient's visit.

Panel 816 shows that the patient's use of the audiovisual device 206 to access the healthcare database 212 to view his medical records continues. As shown in panel 816, the system 100 provides further information responsive to patient's request by outputting information on the display device associated with his audiovisual device 206. Specifically, the system outputs list of actions 820 that the patient is to take in connection with his prescribed treatment.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the invention. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

According to exemplary embodiments, computer-implemented methods, systems and computer-readable media having instructions stored thereon may cause a processor to perform steps for managing clinical and emergency room workflows and accessing, managing and updating patient data records such as appointment records, electronic medical records, personal health records and other healthcare-related patient records. Clinics, hospitals, and emergency rooms sometimes utilize workflows to follow healthcare processes for managing care and the various departments, functions, equipment within the clinical setting. However, this solution utilizes clinical workflow management functionality along with the above-described audiovisual input/output device 206 and analytics programs and data sets to coordinate key functions in managing workflows and patient data.

According to the present disclosure, accessing the patient's data records may follow authentication of the patient's identity using image recognition during a healthcare-related encounter between the patient and personnel at the patient facility. Image recognition involves capturing an image and/or a video of the patient in real time during the encounter, e.g., using the audiovisual input/output device 206 worn by personnel, and matching features of the patient with stored image and/or video data for the patient. Such features may include facial features, eye color, hair color and/or skin color.

As described herein, the audiovisual input/output device 206 may further include a display device viewable by the healthcare professional. During the patient recognition process, a status of the recognition process may be displayed on the display device. Instructions may additionally or alternatively be provided on the display device or via an audio link available to the healthcare professional for facilitating patient recognition, such as instructions for capturing or re-capturing an image and/or video of the patient. Once the patient's identity is determined, the authentication process may be complete. In other implementations, the healthcare professional may additionally request that the patient confirm their identity with an audible response to complete the authentication process. Other modes of authentication of the patient's identity may be used alone or in combination with the above-described patient recognition processes. For example, finger print or retinal scans or password authentication methods are within the scope of the present disclosure. Upon authenticating the patient's identity, the patient's data records may be accessed by authorized personnel.

The audio conversation and video capture of the patient, healthcare professional, and any third parties present during the encounter may be recorded to log the episodes for future reference.

The patient's data records may be reviewed and modified using a variety of data entry approaches including via typing (e.g., using a keyboard, tablet, mobile device), entering selections (e.g., via mouse, touchscreen), and audio cues and/or video cues, e.g., using the audiovisual input/output device 206. In a particular approach, audio voice commands and/or key words recognized by the system may be used to initiate modification of the patient's data records (e.g., using the NLP module 222 and its associated functionalities). Voice commands may include actionable commands such as update, delete, order, prescribe; and key words may identify fields or areas of the patient data record to be modified based on the command, e.g., health history, symptoms, conditions, prescriptions. In some implementations, the content used to modify the patient's data records may be speech that follows or that precedes the commands and/or key words. For example, because the encounter may be recorded from start to finish, virtually any speech-derived data may be used in updating the patient's data record. Further, speaker identification may be utilized to assign speakers to their relative sections of text in the conversation, similar to scripts in a play. Further, analytics may be utilized to identify the mood or emotions of the patient and provider during various points of the conversation to evaluate the interaction for identification of healthcare professional coaching purposes, patient follow-up, best practices identification and other purposes.

Modifying the patient's data records may follow an ordered sequence of steps, such as according to a workflow associated with the patient encounter. During such sequence of steps, the patient may interact with a number of healthcare professionals, each of which may have a designated role in the workflow (e.g., check-in/admitting, labs, nursing/rooming, and physician visit) and a pre-defined authorization level that enables the healthcare professional access and edit rights to the patient's data records. In some implementations, the healthcare professional's voice may be associated with a profile of the healthcare professional (e.g., name, credentials, authorizations) and only portions of the patient's data records and associated workflows may be updated according to an authorization level of the healthcare professional. In certain other implementations, a medical record may be updated by an unauthorized user, but the information is flagged, segregated, or otherwise isolated from the rest of the record until an authorized user gives correct authorization. The authorized user may be prompted to give authorization by receiving an alert, request, or other prompt to permit integration of the information. For example, an administrative staff recognized by her voice may be authorized to update the patient's appointment record, insurance information and administrative data but may not be authorized to add patient symptoms and conditions into the patient's data records. The administrative staff may attempt to add a symptom to the patient's data records. That addition may be allowed, but placed in a special area of, or away from, the rest of the patient data records, which may indicate that the information came from an unauthorized source. An authorized user (such as a doctor associated with the patient record) may receive a prompt regarding whether to integrate or delete the unauthorized information. The user may also indicate that the information should remain isolated. The prompt may occur at various times, including immediately when the unauthorized modification was made and/or the next time that the record is accessed by an authorized user.

If the information is integrated, it may be made indistinguishable from information entered by an authorized user. In certain implementations, the information may bear an indication that it was entered by an unauthorized user. In another example, a physician recognized by her voice may be authorized to update the patient's data records with symptoms, conditions, orders, prescriptions and follow-up instructions (e.g., instructions for a next patient appointment). As another example, voice recognition may be used to identify the speaker of information during a note taking or recording process. This recognition may cause the notes associated with the patient to be annotated based on the speaker. For example, the system may use the recognition to separate or create structured data based on who is speaking (e.g. as may be found in a screenplay). The separation based on who is speaking may also be useful to avoid incorrect notes. For example, this may prevent information spoken by the patient to be incorrectly noted as something that the doctor had said.

In some implementations, the audiovisual input/output device 206 employed by personnel may be authenticated by the personnel prior to the patient encounter, and only those patient workflows available to the personnel based on their authorization level may be accessed. As the patient moves through their encounter at various stations, specific portions of the patient's data records may be updated by personnel based on personnel authorization and the workflows may proceed according to an ordered sequence based on the patient's interactions with authorized personnel.

In a particular example, each participant in the encounter may be identified and the respective participants' verbal contributions may be associated with a given participant. The entire exchange or portions thereof may be added to the patient's data records. In some cases, the entire exchange may be stored as audio data, may be translated into text and stored, or both, as described herein. In another example, a healthcare professional may verbalize commands and/or keywords instructing that the patient's data record be modified based on the patient's verbal contribution during the encounter.

According to certain implementations, evidence-based medicine, HEDIS, and other business rules may be leveraged to identify gaps in care, high risk medication warnings, low-cost alternative medications and other types of point of care information and present these as alerts to the healthcare professional as part of the workflow. This may facilitate the closure of gaps in care during the encounter, such as by having the patient visit the lab for a cholesterol screening blood draw or by warning the doctor or other personnel that the combination of drugs being prescribed pose a high risk for causing certain conditions when used together. Another example may be offering Simvastatin instead of Lipitor as a low cost alternative based on a patient's health plan formulary and reminding them to prescribe 90 rather than 30 day fills for chronic conditions to reduce cost and improve medication adherence.

Healthcare professionals often need to search for additional healthcare information as they try to find information for themselves or their patients related to conditions or care for the patient.

Healthcare professionals may need to consult with specialists, primary care physicians, and others during the course of providing care. This solution would allow them to consult and collaborate with these other parties real-time during the patient visit. For instance, the audiovisual input/output device 206 may be communicatively coupled to other healthcare professionals' devices to enable the person wearing the audiovisual input/output device 206 to consult and collaborate with other professionals during the patient encounter.

Healthcare professionals may need to translate for patients speaking other languages. This solution could translate communications to be spoken to the patient and communications spoken by the patient to be displayed on the screen or spoken by the audio application.

In a further example, where the patient verbally self-reports symptoms and/or conditions to a healthcare professional during the encounter, but the healthcare professional, such as an administrative assistant, does not have authorization to update the patient's data record with symptoms and conditions, the healthcare professional may verbalize commands and/or keywords that notify a physician, or other healthcare professional with the requisite level of authorization, of the patient's self-reported symptoms and conditions. This may result in the physician being alerted (e.g., via the audiovisual input/output device 206) of the patient-reported information, and the physician may authorize entry of such information. In addition or alternatively, the physician may review the recording of the patient's self-reported information and may verbalize commands and/or keywords for updating the patient's data record using the recording. In addition or alternatively, the physician may verbalize commands and/or keywords for updating the data record using the physician's own words. This may facilitate entry of medical terminology into the data records.

As described above, natural language processing (NLP) may be used in accordance with the implementations of the present disclosure. Relevant techniques including LifeCode processor and other NLP engines are described, for example, in U.S. Pat. No. 6,915,254 to Daniel T. Heinze and Mark L. Morsch, AUTOMATICALLY ASSIGNING MEDICAL CODES USING NATURAL LANGUAGE PROCESSING, issued Jul. 5, 2005, and U.S. Pat. No. 7,908,552 to the same inventors, MERE-PARSING WITH BOUNDARY AND SEMANTIC DRIVEN SCOPING, issued Mar. 15, 2011, each of which is incorporated by reference herein, in the entirety. Additional relevant techniques are described in U.S. patent application Ser. No. 11/735,264, filed Apr. 13, 2007, MULTI-MAGNITUDINAL VECTORS WITH RESOLUTION BASED ON SOURCE VECTOR FEATURES; U.S. patent application Ser. No. 12/185,754, filed Aug. 4, 2008, VISUALIZING THE DOCUMENTATION AND CODING OF SURGICAL PROCEDURES; U.S. patent application Ser. No. 09/364,930, AUTOMATICALLY ASSIGNING MEDICAL CODES USING NATURAL LANGUAGE PROCESSING, filed Jul. 30, 1999, issuing Jul. 5, 2005 as U.S. Pat. No. 6,915,254; U.S. patent application Ser. No. 11/735,278, MERE-PARSING WITH BOUNDARY AND SEMANTIC DRIVEN SCOPING, filed Apr. 13, 2007, issuing Mar. 15, 2011 as U.S. Pat. No. 7,908,552; U.S. patent application Ser. No. 13/016,764, MERE-PARSING WITH BOUNDARY AND SEMANTIC DRIVEN SCOPING, filed Jan. 28, 2011; U.S. patent application Ser. No.; and U.S. patent application Ser. No. 14/019,489, AUTOMATED CLINICAL INDICATOR RECOGNITION WITH NATURAL LANGUAGE PROCESSING, filed Sep. 5, 2013 each of which is also incorporated by reference herein, in their entirety.

NLP may be used to convert received information or data into structured data. Structured data may include data that has been split, annotated, rearranged, or otherwise altered to impart a structure or scheme that makes the information more understandable or useful to components of the system 100 and/or users. For example, speech-to-text data may include voice data from a patient listing symptoms, such as "My tummy hurts and I threw up." A NLP module (such as NLP module 222) may process and understand the text and convert it to a standardized format, such as "abdominal pain, vomiting." In addition, the NLP module may recognize this information as symptoms and include a tag or other indication that a particular part of the text includes symptoms. The structure may be implemented using a markup scheme or language, such as XML. As another example, the structured data may include an indication of the speaker of the text. The structure of the data may facilitate integration of the information into appropriate sections of medical records. The structure may also be used to facilitate a comparison between received data and existing patient records. For example, the NLP module may convert a verbal indication of a prescription (such as, a doctor telling the patient that the he or she is prescribing a particular medication) into structured data. The structured data may then be compared against the patient's medical record to determine whether there are any issues with the prescription. For example, the patient may have used the prescription in the past and suffered negative side effects.

In certain embodiments of systems and methods described herein, there may be a log-in process used by the device 204, 206 to enable access to services provided by the system 100 (e.g., a patient management system that provides access to, among other things, a list of patients, patient information, and medical records). In some implementations, services may be accessible only from a particular network (e.g., a network private to a particular hospital) or be publicly accessible, which may be useful for paramedics or other users attempting to log in remotely. In certain instances, the log-in process may involve a user directing a browser or other tool to access a hosted service (e.g. a website hosted at the server 120). The browser may be run on the device 204, 206 itself and/or on a different computing device. At the login page, the user may be prompted to enter authentication credentials, which may include a username, password, biometrics, and/or other credentials. The credentials may then be verified against user credentials stored at, for example, the database 116. The credentials may be used to associate the user with the particular device 204, 206. In certain implementations, the credentials may include visual, audio, or other kinds of biometric authentication, such as voice recognition, facial recognition, retina identification, and fingerprint identification. The biometric authentication may enable the device to automatically associate the user with the device without the requiring the user to enter additional authentication credentials.

After logging in, the service may determine which locations (e.g. a hospital) the user has privileges to access based on the user's authentication credentials and information stored about the user within the system 100. Once the user selects the location, a code may be displayed that, when entered into the device 204, 206, will enable the device 204, 206 to synchronize, associate, authenticate, or otherwise register with the system 100. This code may be described as a synchronization code. To facilitate entry of the code on a device, the code may be presented as a machine-readable code such as a barcode or a matrix barcode (e.g. a QR code). In certain implementations, the code may be presented as a device-recognizable audio tone that can be received and understood by the device 204, 206. The device 204, 206 may capture this code using a camera, microphone, or other means so the user does not need to enter the code into the device by hand.

In certain implementations, once the device 204, 206 has been registered with the system 100, the system 100 may monitor the amount of data traffic to and from the device 204, 206. Instead of or in addition to monitoring the data traffic itself, the amount of data traffic may be used for billing purposes. For example, the hospital associated with the device 204, 206 may be billed based on its use of the system 100 for patient management. For instance, the hospital may be charged per gigabyte or per terabyte of data used by its devices. By inspecting only the amount of data traffic rather than the data itself, the privacy of patients may be better protected.

FIGS. 9A-D illustrate an implementation of a patient management system according to certain embodiments. For example, the device 204, 206 may be used within an emergency department of a hospital to identify patients, determine the order in which patients are to be treated, and identify key information about the patient to facilitate appropriate treatment. For instance, using the device 204, 206, a user may call up a screen (such as via a head-mounted display) that shows or an audio cue that describes the number of patients in a particular stage of the emergency department's patient management workflow. While the implementation is illustrated in the context of an emergency department, the systems and methods disclosed may be utilized in other patient management contexts.

FIG. 9A illustrates an embodiment of a main menu screen 902, including an indication of: various stages of patient flow within the emergency department (e.g., from triage to observation), the number of patients in each stage, and an indication of the current longest wait time for a patient in that stage. The information in this screen 902 may be user-selectable, such as via voice command, tracked eye command, touch command, and other input. As a specific example, the device 204 may have a touch strip for input. If the user taps the touch strip, the device 204 may display a selection highlighter and sliding a finger along the strip may cause the selection to scroll or change. The device 204 may be configured to distinguish between a quick tap and a long press. For example, a tap could cause a highlighted item to be selected and a long press could be used to cause the device to reorder a list (e.g. in alphabetical order). The selection may enable the user to retrieve more information about, for example, each stage. As illustrated, the stage "Lab Results" has been selected.

FIG. 9B illustrates an example patient select screen 904 displayed responsive to receiving the selection of the "Lab Results" stage of screen 902. The patient select screen 904 may show a list of the names of the patients, stage-related information (in this case, the lab results for which the patient is waiting), and how long each patient has been waiting. Certain implementations may also include a mark or symbol by each patient's name, such as circles, stars, checks, exclamation marks, and other symbols. The mark or symbol may indicate a status of the patient. For example, an exclamation mark may indicate that the patient needs immediate attention. As another example, a question mark may indicate that a patient has a question for a doctor. The patients listed may also have color-coded indications. For example, one or more of the portions of the screen may be colored to indicate that the patient has been triaged into a high-risk category. As another example, elapsed wait time may be color coded to indicate how long the patient has been waiting.

Like the previous screen, the information contained within this screen 904 may be user-selectable. A selection may cause the device 206 to retrieve more information about, for example, each patient. As illustrated, the patient "Bob Johnson" has been selected.

FIG. 9C illustrates a patient information screen 906. This screen 906 may be displayed following the section of a patient from the patient select screen 904. Information in this screen 906 may also be user-selectable. As illustrated, the "ADDITIONAL OPTIONS" choice has been selected.

The patient information screen 906 illustrates more information about the selected patient than the patient select screen 904. This information may include the patient's picture, name, gender, age, arrival time, length of wait, and/or status. The screen 906 may also include alert information for the patient. This may include information of which healthcare provider should be made aware. For example, as illustrated, the alert notes that the patient has a latex allergy. This information may be used to minimize the risk of allergic reactions. For instance, the user may notice the alert information and choose alternatives to latex gloves. In another instance, the device 206 may detect that the user is about to engage in an action that may place the patient at risk and alert the user, such as playing an alert tone and/or flashing a message on the screen. The detection may be made by comparing received data (e.g., audio, image, or other data) with information contained with the medical record of a patient. For example, the device 206 may use optical character recognition or speech recognition to create text data, which is then translated into structured data using natural language processing. The structured data may facilitate a comparison with the patient's medical record to determine that the user is prescribing or reaching for a drug to which the patient has an allergy. This comparison may then be used to generate a message to warn the user that the user is performing an action that may harm the patient.

As another example, alert information may be used to eliminate gaps in patient care. For instance, the system 100 may determine that the patient is due for or will soon be due for a cholesterol screening, mammogram or other appointment. In response, the device 204, 206 may alert the user. In response, the user may remind the patient of the upcoming event. In some implementations, the system 100 may enable the user to schedule or reschedule the appointment for the same day so that the other appointment can be performed while the patient is already at the care facility. This may be useful for eliminating gaps in care and decreasing the need for repeat trips by the patient.

The user may manage patient workflow using information made available by the above screens. For example, the user may identify that a patient has been waiting a longer-than-desired time for results. Based on the wait time, the user may decide to follow up with the patient. This may include, for example, using that patient's picture to locate the patient in a waiting room and inform the patient of the status of their expected wait time or other information. In certain implementations, the user may be able to log information about such patient encounters.

FIG. 9D illustrates an options screen 908 related to a patient. As illustrated, the screen 908 presents options for indicating that the patient has received feedback or is waiting for feedback; however, other selections are also possible. Selections made by the user may update information relating to the patient. For example, as illustrated, the "Received Feedback" selection has been selected. In some implementations, this selection may change how the patient's wait time is displayed. For example, the wait time may be changed to be the wait time since last update. In some implementations, an indicator associated with the wait time may change. For example, the wait time may be a high number, but a particular color may be used to indicate that the particular patient's wait time is less of a priority than it otherwise would have been (e.g. showing the wait time in green rather than red). In other implementations, the indicator may be a flag or other marker showing the change in status. In still other implementations, the time that the user received feedback is logged with the system. The logging may be used to ensure compliance with the system by staff members. For example, a hospital may set a policy that patients should not wait longer than twenty minutes without receiving feedback regarding the status of his or her appointment. The logs may be used to track whether the feedback is being provided to the patients.

A "Waiting for feedback" option is also selectable in the illustrated embodiment. Selecting this option may cause the associated patient to be marked as waiting for feedback. This may be useful in situations where, for example, the patient is waiting for an answer to a particular question. This option may change various display options relating to the patient. For example, when the patient is waiting for feedback, the time that the option was selected may be displayed in red. If the patient subsequently receives feedback, then the marker may be removed or modified.

In another example implementation, the device 204, 206 may use patient-recognition technology (e.g. facial or audio recognition) to determine the identity of a patient without the patient needing to give his or her name. For example, the device 204, 206 may detect that the user is looking at a particular patient and automatically begin the process of recognizing the patient. The device 204, 206 may also be configured to retrieve conversation-relevant information regarding the patient. For instance, the patient may approach the user and ask about the check-in status of his or her appointment. The device 204, 206 may automatically recognize the patient and retrieve from the system or the patient's medical record an estimated wait time for the patient's appointment. This process may be performed without the user needing to ask the patient for his or her name or other identifying information.

What is claimed is:

1. A method for entering medical information with integrated data entry and workflow during an interaction with a patient, the method comprising:

providing an alert from an audiovisual input/output device of a computing device to move the patient from a first station to a second station;

receiving a special-purpose wearable computing device configured to enable a user at the second station to input and retrieve medical information without breaking line-of-sight interaction with the patient, wherein the user is wearing the special-purpose wearable computing device and the user is distinct from the patient;

authenticating the user at the second station;

after authenticating the user at the second station, receiving information relating to the patient from a head-mounted display of the special-purpose wearable computing device; and causing a record of the patient to be updated by speaking a command using a natural language processing module and an optical character recognition service, the natural language processing module configured to recognize the command and extract certain information from data received from one or more inputs of the special-purpose wearable computing device, the optical character recognition service configured to convert images contained in the data received from the one or more inputs of the special-purpose wearable computing device into computer readable text;

wherein causing a record of the patient to be updated comprises isolating the data received from one or more inputs responsive to determining that the user is not authorized to update the medical record, sending an authorization request to an authorized user, and integrating the data received from one or more inputs responsive to receiving authorization from the authorized user;

wherein the receiving and causing steps are performed without the user breaking line-of-sight interaction with the patient.

2. The method of claim 1, wherein the association is performed automatically by the special-purpose wearable computing device using an audio or visual characteristic of the user received by the special-purpose wearable computing device.

3. The method of claim 1, wherein the information is received using visual information regarding the patient provided to a camera of the special-purpose wearable computing device.

4. The method of claim 1, wherein the information is received responsive to audio information received from a microphone of the special-purpose wearable computing device.

5. The method of claim 1, wherein the received information is a patient alert generated or identified using an event during the interaction.

6. The method of claim 1, wherein the record comprises one or more types of information selected from a group comprising: a check-in status of the patient, an address of the patient, a symptom of the patient, a next appointment of the patient or a vital sign of the patient.

7. The method of claim 1, wherein the information received comprises one or more types of information selected from a group comprising: an identity of the patient, an allergy of the patient, an appointment information of the patient or a next stop for the patient.

8. A method for facilitating an improved interaction between a user and a patient, the method comprising:

providing an alert from an audiovisual input/output device of a computing device to move the patient from a first station to a second station;

authenticating the user at the second station with a special-purpose wearable computing device, wherein the user is wearing the special-purpose wearable computing device and the user is distinct from the patient;

after authenticating the user at the second station, receiving image data from the special-purpose wearable computing device;

converting the images contained in the image data into computer readable text;

after authenticating the user at the second station, receiving voice data from the special-purpose wearable computing device worn by the user;

converting the voice data into text data;

translating the computer readable text and the text data to structured data using natural language processing; and updating a medical record of the patient using the structured data, wherein updating the medical record comprises:

isolating the structured data responsive to determining that the speaker is not authorized to update the medical record;

sending an authorization request to an authorized user; and integrating the structured data responsive to receiving authorization from the authorized user.

9. The method of claim 8, further comprising determining an identity of a speaker of the voice data, wherein translating the text data to structured data accounts for the identity of the speaker.

10. The method of claim 8, further comprising comparing the structured data with the medical record and providing a warning to the user via the special-purpose wearable computing device using the comparison.

11. The method of claim 10, wherein the warning comprises an indication that the user is performing an action that will harm the patient.

12. The method of claim 8, further comprising generating a workflow ticket using the structured data.

13. A method for improving the flow of patients through a hospital, the method comprising:

providing an alert from an audiovisual input/output device a computing device to move the patient from a first station to a second station;

authenticating a user at the second station with a special-purpose wearable computing device by prompting the user to enter one or more authentication credentials, wherein the user is wearing the special-purpose wearable computing device and the user is distinct from the patient;

providing a list of patients to a head-mounted display of the special-purpose wearable computing device worn by a user;

receiving from the special-purpose wearable computing device a selection of a patient from the list of patients;

after authenticating the user at the second station, providing patient information at the display responsive to receiving the selection, wherein the patient information comprises an image of the patient usable by the user to locate the patient;

receiving data regarding an interaction between the user and the patient; and updating a record associated with the patient with the received data using a natural language processing module and an optical character recognition service, the natural language processing module configured to recognize the command and extract certain information from data received from one or more inputs of the special-purpose wearable computing device, the optical character recognition service configured to convert images contained in the data received from the one or more inputs of the special-purpose wearable computing device into computer readable text wherein updating a record associated with the patient comprises isolating the received data responsive to determining that the user is not authorized to update the medical record, sending an authorization request to an authorized user, and integrating the received data responsive to receiving authorization from the authorized user.

14. The method of claim 13, wherein the list of patients comprises: a name of the patient and a wait time of the patient.

15. The method of claim 13, wherein the data regarding the interaction is an indication that the patient received feedback from the user.

16. The method of claim 13, wherein updating the record is responsive to determining that the user has authorization to update the record.

17. The method of claim 13, further comprising: entering login credentials to a second computing device, receiving a synchronization code at the second computing device, and synchronizing the special-purpose wearable computing device with a patient management system using the code.

18. The method of claim 17, wherein the patient management system comprises the list of patients, the patient information, and the record.

\* \* \* \* \*